(12) United States Patent
Mhajna et al.

(10) Patent No.: US 11,877,834 B2
(45) Date of Patent: Jan. 23, 2024

(54) SYSTEMS, APPARATUSES AND METHODS FOR SENSING FETAL ACTIVITY

(71) Applicant: Nuvo Group Ltd., Tel Aviv (IL)

(72) Inventors: Muhammad Mhajna, Tel Aviv (IL); Oren Oz, Modiin (IL)

(73) Assignee: NUVO GROUP LTD., Tel Aviv (IL)

( * ) Notice: Subject to any disclaimer, the term of this patent is extended or adjusted under 35 U.S.C. 154(b) by 834 days.

(21) Appl. No.: 16/969,106

(22) PCT Filed: Feb. 11, 2019

(86) PCT No.: PCT/US2019/017537
§ 371 (c)(1),
(2) Date: Aug. 11, 2020

(87) PCT Pub. No.: WO2019/157463
PCT Pub. Date: Aug. 15, 2019

(65) Prior Publication Data
US 2021/0030288 A1 Feb. 4, 2021

Related U.S. Application Data

(60) Provisional application No. 62/629,510, filed on Feb. 12, 2018.

(51) Int. Cl.
*A61B 5/024* (2006.01)
*A61B 5/0255* (2006.01)
(Continued)

(52) U.S. Cl.
CPC ........ *A61B 5/02411* (2013.01); *A61B 5/0255* (2013.01); *A61B 5/02444* (2013.01);
(Continued)

(58) Field of Classification Search
None
See application file for complete search history.

(56) References Cited

U.S. PATENT DOCUMENTS

2016/0270670 A1 9/2016 Oz et al.
2017/0007142 A1 1/2017 Oz et al.
2017/0156607 A1 6/2017 Oz et al.

OTHER PUBLICATIONS

Venkata et al. "Of Feature Selection and Classification Algorithms for Phonocardiography Signal", IJAER, 2014, pp. 26739-26754.*
(Continued)

*Primary Examiner* — Li Wu Chang
(74) *Attorney, Agent, or Firm* — Greenberg Traurig, LLP

(57) ABSTRACT

A method includes receiving a plurality of raw PCG data inputs; applying at least one binary classification technique to each of the raw PCG data inputs to generate a respective plurality of filtered PCG data inputs; applying at least one divide-and-conquer algorithm to detect heartbeat compartments in each of the plurality of the filtered PCG data inputs based, at least on part, on assumptions that noise signals and S1-S2 alternation acoustic signals are non-stationary over a one-minute time interval; classifying each compartment of the heartbeat compartments in each of the plurality of the filtered PCG data input as a maternal compartment or a fetal compartment based at least on a plurality of referenced maternal QRS positions; combining a plurality of maternal compartments to identify at least one actual maternal heartbeat; combining a plurality of fetal compartments to identify at least one actual fetal heartbeat.

16 Claims, 42 Drawing Sheets

(51) Int. Cl.
  *A61B 5/00* (2006.01)
  *A61B 5/0245* (2006.01)
(52) U.S. Cl.
  CPC ............ *A61B 5/725* (2013.01); *A61B 5/7264* (2013.01); *A61B 5/0245* (2013.01); *A61B 2562/0204* (2013.01)

(56) References Cited

OTHER PUBLICATIONS

Adithya et al. "Trends in fetal monitoring through phonocardiography: Challenges and future directions", Biomedical Signal Processing and Control, 2017, pp. 289-305.*

International Search Report and Written Opinion from International Patent Application No. PCT/US2019/017537 dated May 9, 2019.

Jezewski et al., "Is Abdominal Fetal Electrocardiogram an Alternative to Doppler Ultrasound for FHR Variability Evaluation?", Frontiers in Physiology, May 2017, vol. 8, Article 305.

Krupa et al., "Antepartum fetal heart rate feature extraction and classification using empirical mode decomposition and support vector machine", BioMedical Engineering OnLine, 2011, 10:6.

* cited by examiner

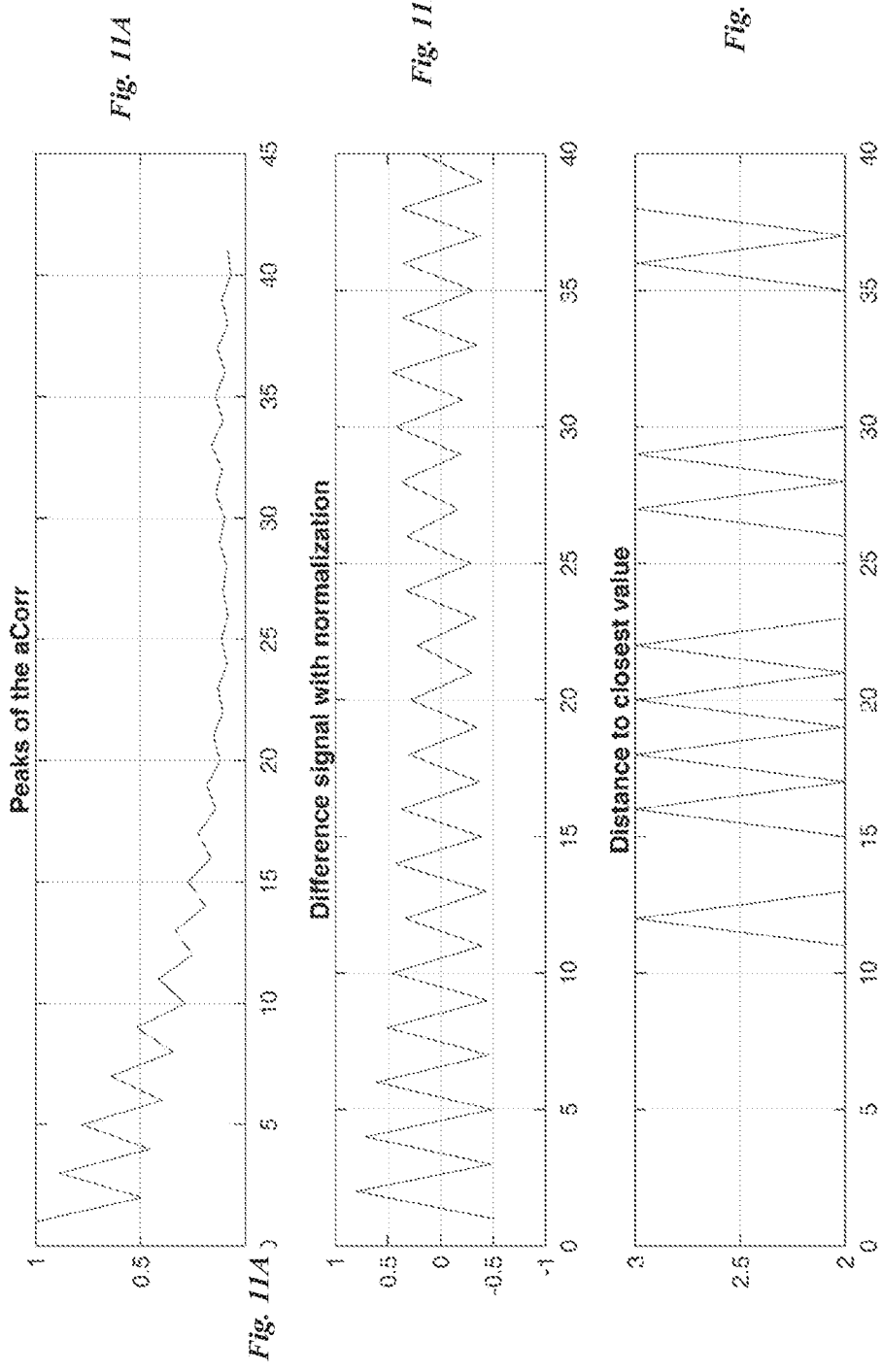

SYSTEMS, APPARATUSES AND METHODS FOR SENSING FETAL ACTIVITY

CROSS-REFERENCE

This international patent application relates to and claims the benefit of commonly-owned, U.S. Provisional Patent Application No. 62/629,510, entitled "SYSTEMS, APPARATUSES AND METHODS FOR SENSING FETAL ACTIVITY," filed Feb. 12, 2018, the contents of which are incorporated herein in their entirety.

FIELD OF THE INVENTION

The invention relates generally to systems and methods for monitoring the wellbeing of a fetus by the non-invasive detection and analysis of fetal cardiac activity data.

BACKGROUND

Monitoring fetal cardiac activity can be useful to determine the health of a fetus during pregnancy.

BRIEF DESCRIPTION OF THE DRAWINGS

The present invention can be further explained with reference to the attached drawings, wherein like structures are referred to by like numerals throughout the several views. The drawings shown are not necessarily to scale, with emphasis instead generally being placed upon illustrating the principles of the present invention. Therefore, specific structural and functional details disclosed herein are not to be interpreted as limiting, but merely as a representative basis for teaching one skilled in the art to variously employ the present invention.

SUMMARY

Figure 1:
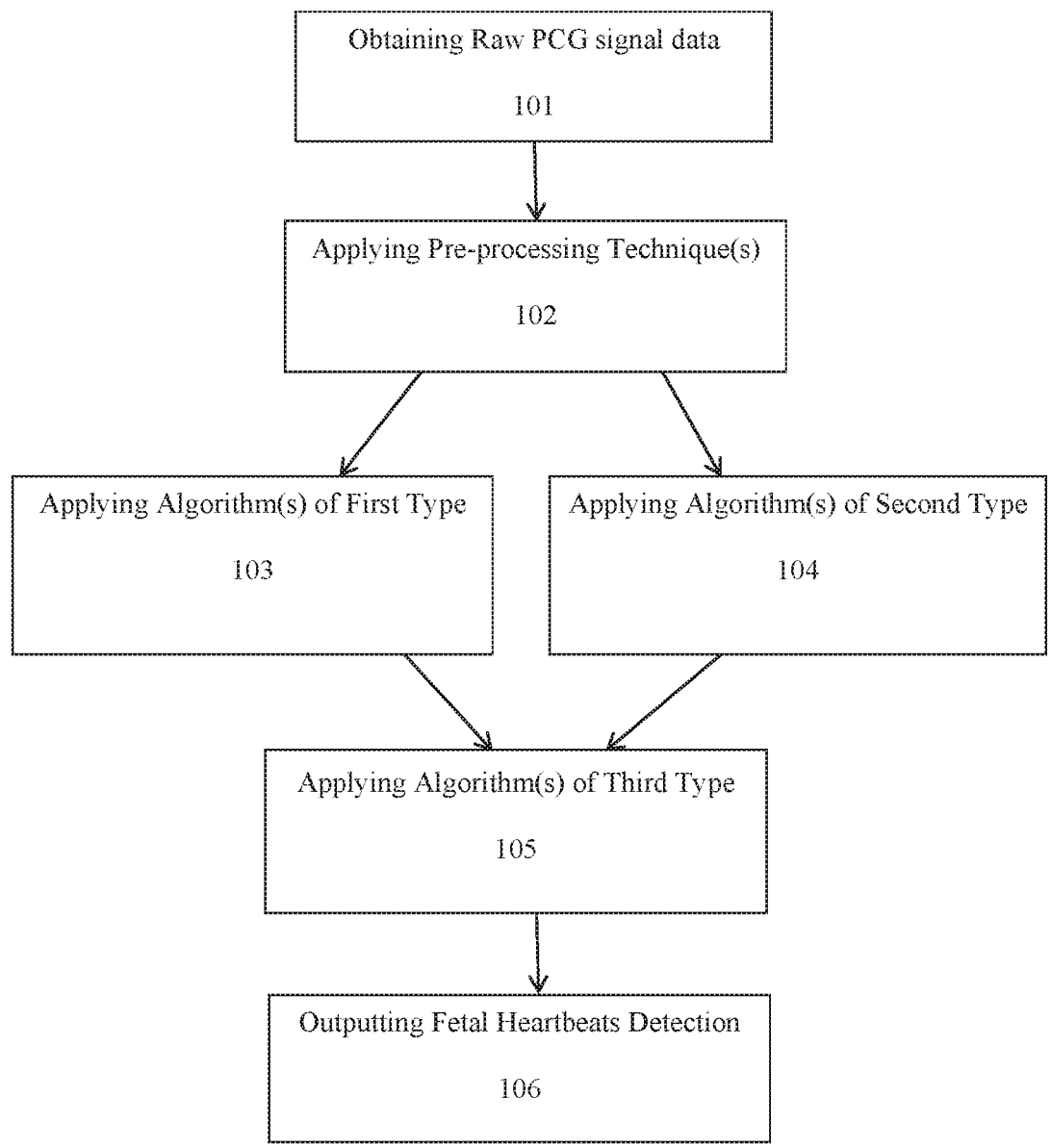
FIG. 1 is a flowchart of an exemplary method.

In an embodiment, a computer-implemented method includes receiving, by at least one computer processor executing specific programmable instructions configured for the method, a plurality of raw phonocardiogram (PCG) data inputs, each of the plurality of raw PCG data inputs being received from a corresponding one of a plurality of acoustic sensors; applying, by the at least one computer processor, at least one binary classification technique to each of the plurality of raw PCG data inputs signals to generate a respective plurality of filtered PCG data inputs, by filtering each respective raw PCG data input based, at least in part, on one or more of: i) a root-mean-square (RMS) value of each respective raw PCG data input, ii) a RMS value of a first derivative of each respective raw PCG data input, iii) a variance value of each respective raw PCG data input, and iv) any combination thereof; applying, by the at least one computer processor, at least one divide-and-conquer (Div-Conq) algorithm to detect heartbeat compartments in each of the plurality of the filtered PCG data inputs based, at least on part, on assumptions that noise signals are non-stationary over a one-minute time interval and that S1-S2 alternation acoustic signals are non-stationary over the one-minute time interval; classifying each compartment of the heartbeat compartments in each of the plurality of the filtered PCG data input as a maternal compartment or a fetal compartment based at least on a plurality of referenced maternal QRS positions; combining a plurality of maternal compartments to identify at least one actual maternal heartbeat; combining a plurality of fetal compartments to identify at least one actual fetal heartbeat; and outputting at least one visual indication corresponding to at least one of (a) the at least one actual maternal heartbeat and (b) the at least one actual fetal heartbeat.

In an embodiment, the Div-Conq algorithm includes at least the steps of: i) filtering each of the pre-processed PCG signals using at least one digital filter to generate a plurality of filtered PCG signals, each of the plurality of the filtered PCG signals being generated based on a corresponding one of the pre-processed PCG signals; ii) segmenting each of the filtered PCG signals into PCG signal segments having a predetermined length; iii) detecting compartments in the PCG signal segments, wherein the step of detecting compartments comprises the sub-steps of: a) identifying related beats; b) shifting each beat, related to the beat with the mean RMS energy; c) finding sub-compartments of each beat; and d) linking sub-compartments from different beats using dynamic programming to generate an indication of a heartbeat.

In an embodiment, the predetermined length is 10 seconds. In an embodiment, the compartments include at least one S1, at least one S2, or at least one S1 and at least one S2. In an embodiment, the compartments include at least one of a fetal heartbeat, a maternal heartbeat, and/or both a maternal heartbeat and a fetal heartbeat. In an embodiment, the at least one digital filter includes a complex Hilbert transform filter.

In an embodiment, if more than one group of compartments have been detected, the Div-Conq algorithm further comprises testing the groups of compartments. In an embodiment, the step of testing the groups of compartments includes a mean absolute deviation process.

In an embodiment the step of detecting compartments in the PCG signal segments further comprises the sub-step of dissecting compartments into sub-compartments. In an embodiment, the dissecting compartments into sub-compartments comprises: a) defining a global reference frame; b) aligning sub-compartments; and c) applying a predetermined scoring schema to exclude unacceptable sub-compartments. In an embodiment, the defining a global reference frame is based on mQRS positions. In an embodiment, the defining a global reference frame is based on a best sub-compartment. In an embodiment, the best sub-compartment is identified by a pre-determined scoring. In an embodiment, the unacceptable compartments are identified as compartments having a mean absolute deviation that is greater than a mean absolute deviation threshold. In an embodiment, the mean absolute deviation threshold is 50. In an embodiment, the step of detecting compartments is performed using a binary SVM classifier.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the present invention is directed to detection of fetal heartbeats (FHs) from phonocardiogram (PCG) signals data. Typically, FHs are in a form of a semi-periodic acoustic signal that may be 15-100 Hz in frequency bandwidth and may be similar to maternal signals in amplitude. Typically, the PCG signals data may be contaminated with acoustic noises. In some embodiments, one or more exemplary methodologies of the present invention include processing the obtained, raw PCG signals data to remove at least some portion of acoustic external noises. In some embodiments, one or more exemplary methodologies of the present invention include further removal at least some portion or sufficient portion, which may include removing all, of maternal PCG signal data. In some embodiments, one or more exemplary methodologies of the present invention may be based on an assumption that maternal heartbeats (MHs) may be annotated using electrocardiogram signal (ECG) data.

Specifically, in some embodiments, as detailed in FIG. 1, at step 101, the instant invention is directed to obtaining raw PCG signals data from one or more suitable acoustic sensors that may be positioned in vicinity of a stomach of a pregnant woman (e.g., sensor(s) may be in a belt positioned over the stomach of the pregnant woman). Referring to step 102 of FIG. 1, the instant invention is directed to programming an exemplary computer processor so that the exemplary computer processor applies one or more pre-processing techniques to filter the raw PCG signal data and/or separated raw PCG signal data based on one or more sources (e.g., maternal PCG, fetal PCG, etc.) to yield first transformed (T1) signal data. Referring to step 103 of FIG. 1, the instant invention is directed to programming the exemplary computer processor so that the exemplary computer processor applies one or more algorithms of a first type to further transform the T1 signal data. Referring to step 104 of FIG. 1, the instant invention is directed to programming the exemplary computer processor so that the exemplary computer processor applies one or more algorithms of a second type to also further transform the T1 signal data in parallel with the processing of step 103.

For clarity of disclosure, and not by way of limitation, the detailed description of the invention is divided into the following subsections that describe or illustrate certain features, embodiments or applications of the present invention.

I. Illustrative Examples of Applying one or More Pre-Processing Techniques

In some embodiments, one or more exemplary methodologies of the present invention include programming the exemplary computer processor so that the exemplary computer processor applies one or more pre-processing techniques to filter the raw PCG signal data and/or separated raw PCG signal data based on one or more sources. For example, one exemplary pre-processing technique may be utilizing at least one binary classification technique based, at least in part, on a Support Vector Machine (SVM) classifier. For example, an exemplary SVM classifier model may be a representation of examples as points in space, mapped so that the examples of separate categories are divided by a clear gap that is as wide as possible. New examples are then mapped into that same space and predicted to belong to a category based on which side of the gap they fall. In some embodiments, the exemplary binary classification pre-processing technique of the present invention may be utilizing at least one binary classification to filter and/or separate the raw PCG signal data based, at least in part, on one or more of the following features:

i) a root-mean-square (RMS) value of the raw PCG signal,
ii) a RMS value of the first derivative (RMS of Div) of the raw PCG signal,
iii) a variance value of the raw PCG signal, and
iv) any combination thereof.

In some embodiments, the exemplary binary classification pre-processing technique of the present invention may be executed by utilizing MATLAB® code (MathWorks, Inc., Natick, MA).

Figure 2:
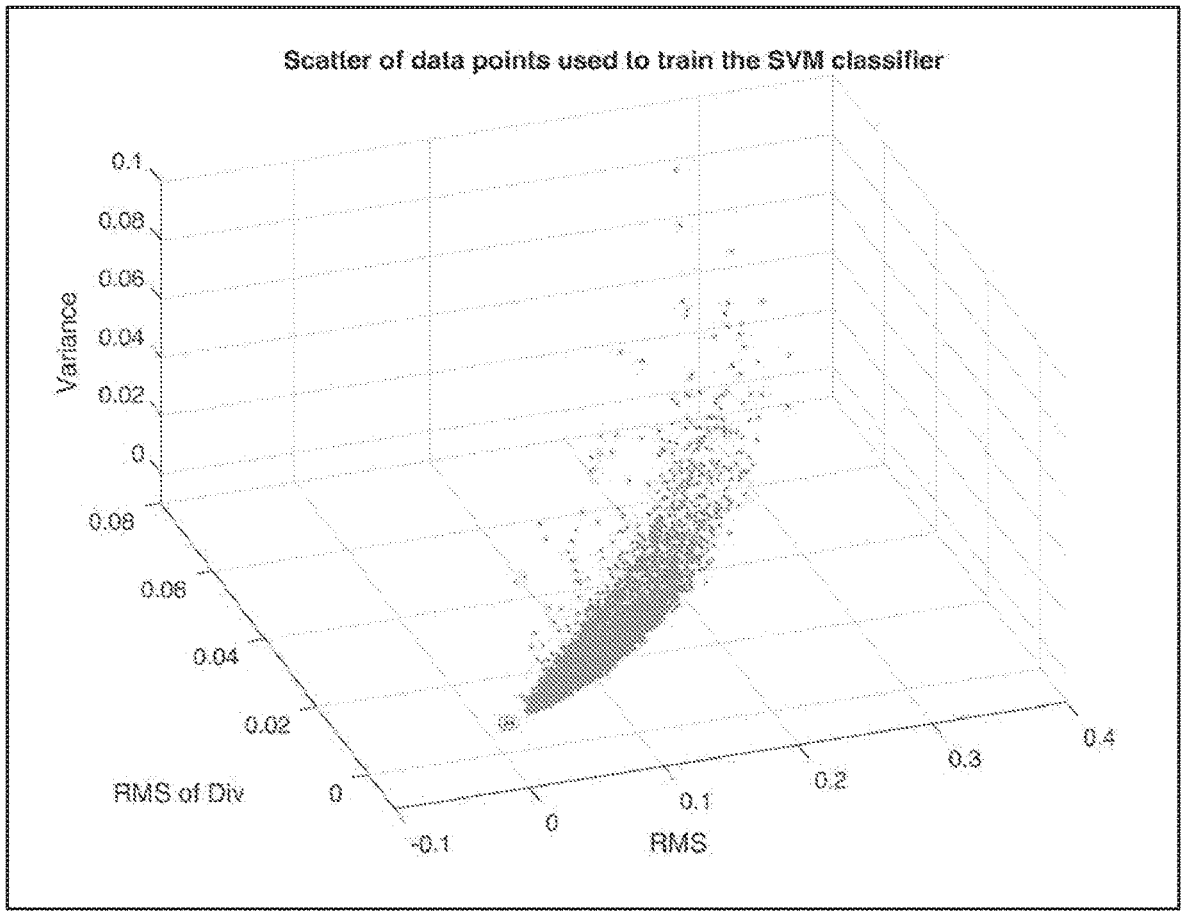
FIG. 2 shows an exemplary collection of data points that might be used to train an exemplary SVM classifier.

FIG. 2 shows an exemplary collection of data points that might be used to train the exemplary SVM classifier of the present invention.

Figure 3:
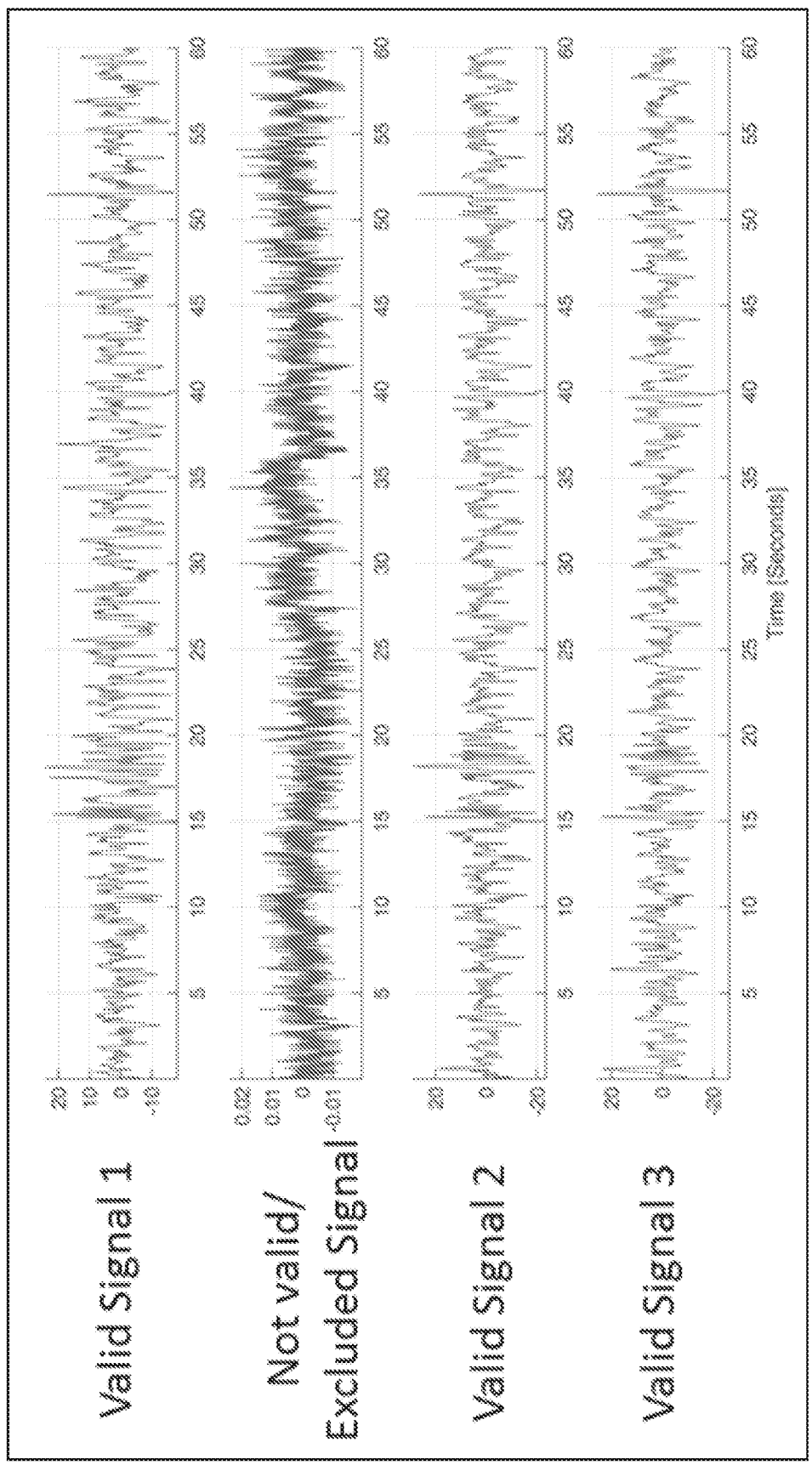
FIG. 3 shows exemplary outputs of the exemplary SVM classifier of the present invention as valid (acceptable) signals 1-3 and an excluded (noise) signal.

FIG. 3 shows exemplary outputs of the exemplary SVM classifier of the present invention as valid (acceptable) signals 1-3 and an excluded (noise) signal. For example, an exemplary processor programmed in accordance with the present invention may determine whether a particular signal is valid or non-valid based on an amplitude and/or frequency. For example, as shown in FIG. 3, the exemplary excluded (noise) signal may be a signal with average RMS amplitude may be below a pre-determined threshold which may be expressed in dB units. For example, in some embodiments, the exemplary pre-determined threshold is 1 db. For example, in some embodiments, the exemplary pre-determined threshold is 5 db. For example, in some embodiments, the exemplary pre-determined threshold is 10 db. For example, in some embodiments, the exemplary pre-determined threshold is 15 db. For example, in some embodiments, the exemplary pre-determined threshold is 20 db.

II. Illustrative Examples of Applying One or More Algorithms of the First Type

In some embodiments, one or more exemplary methodologies of the present invention include programming the exemplary computer processor so that the exemplary computer processor applies one or more algorithms of the first type to further transform the T1 signal data. In some embodiments, one or more algorithms of the first type may include one or more Divide-and-Conquer (Div-Conq) algorithms. In some embodiments, an exemplary Div-Conq algorithm is based, at least in part, on an assumption that (1) noise signal and (2) S1-S2 alternation acoustic signals are non-stationary over the one minute interval. Initially, the execution of the exemplary Div-Conq algorithm may begin with segmenting T1 signals into X second intervals. For purposes of illustration, the following description of applying the exemplary Div-Conq algorithm is based on dividing the T1 signal by a 10 second time interval (time window).

Sub-Step 1

Figure 4:
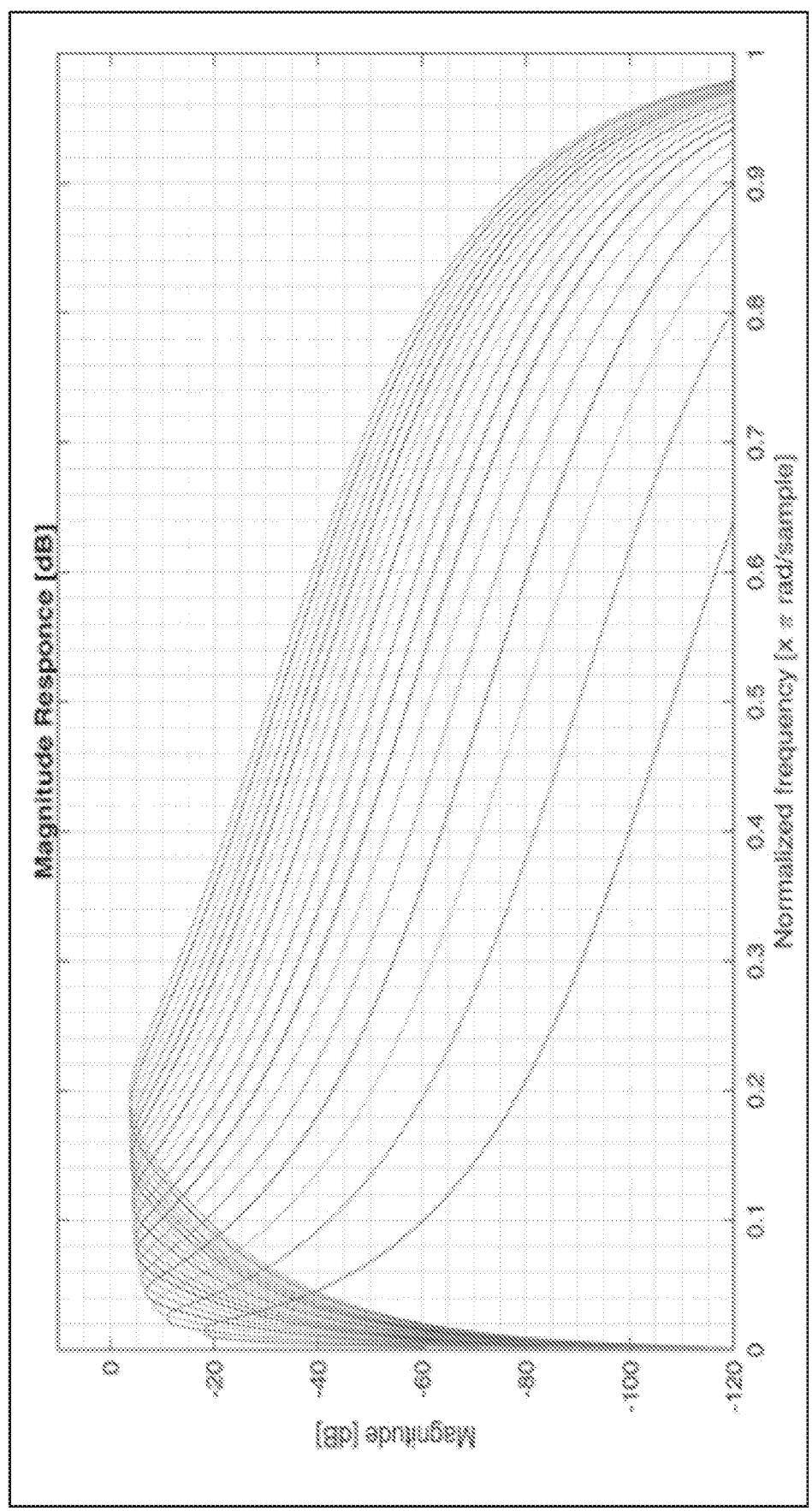
FIG. 4 illustrates an exemplary magnitude response of the exemplary digital filter that may be utilized for the sub-step 1.
Figure 5A:
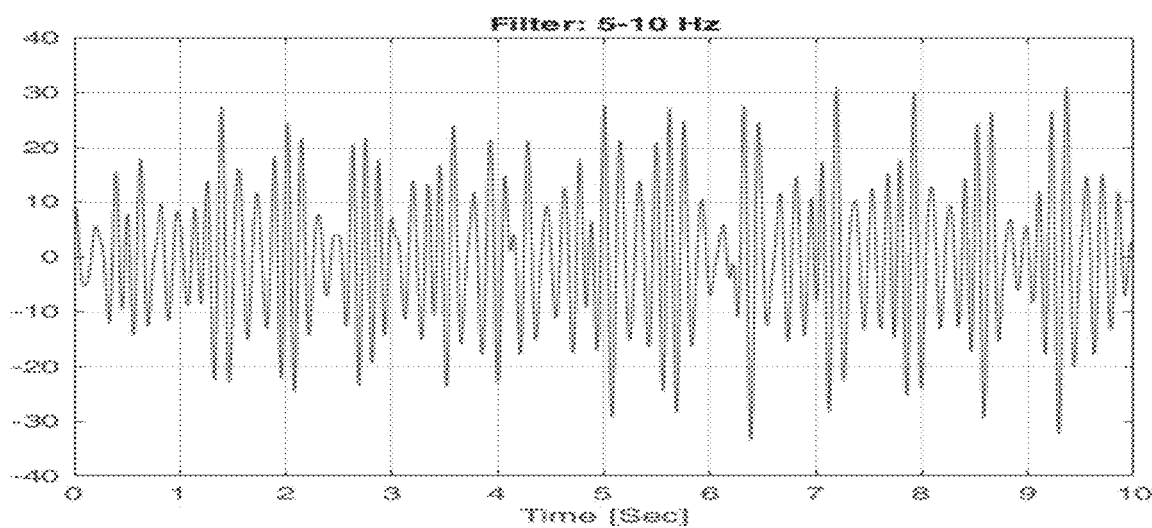
FIGS. 5A-5H show examples of passbands of maternal PCG signal filtered with different filters.
Figure 5B:
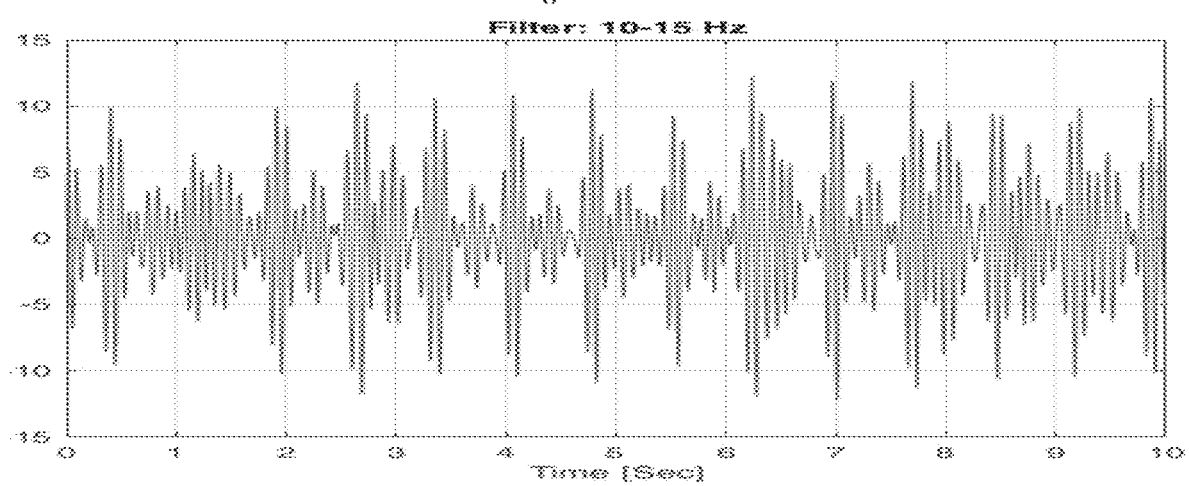
Figure 5C:
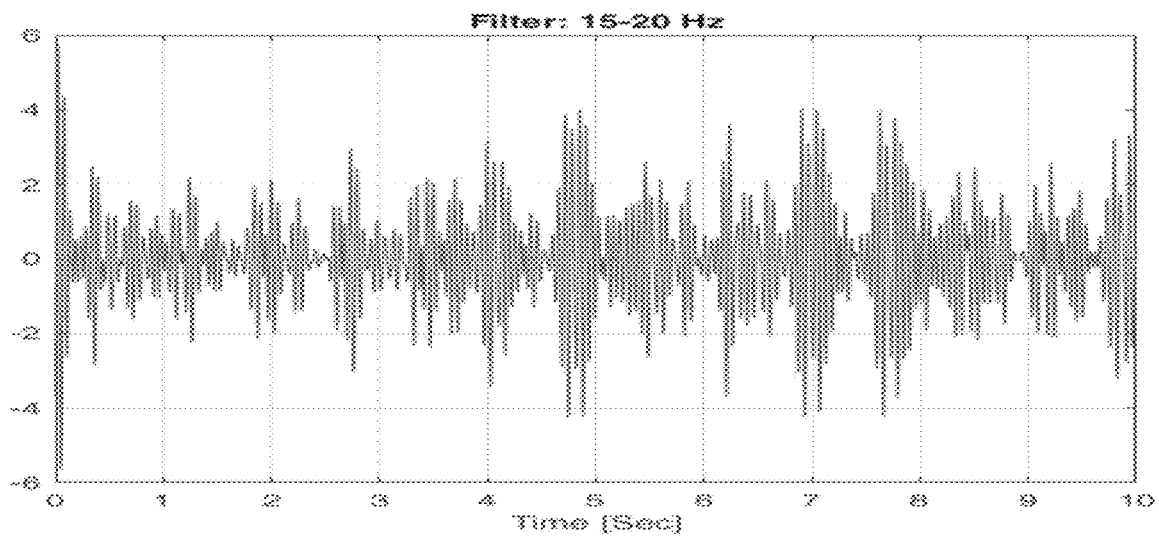
Figure 5D:
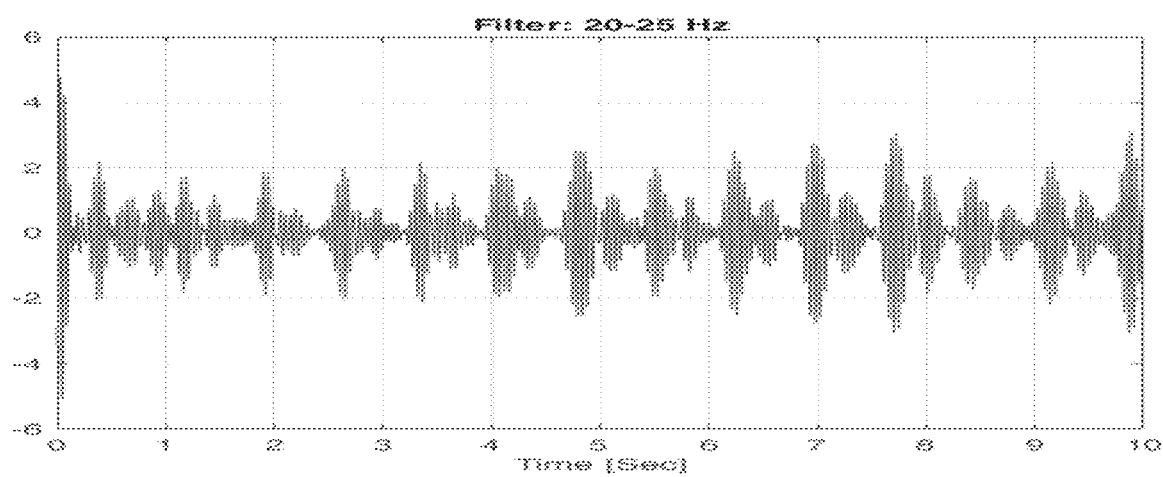
Figure 5E:
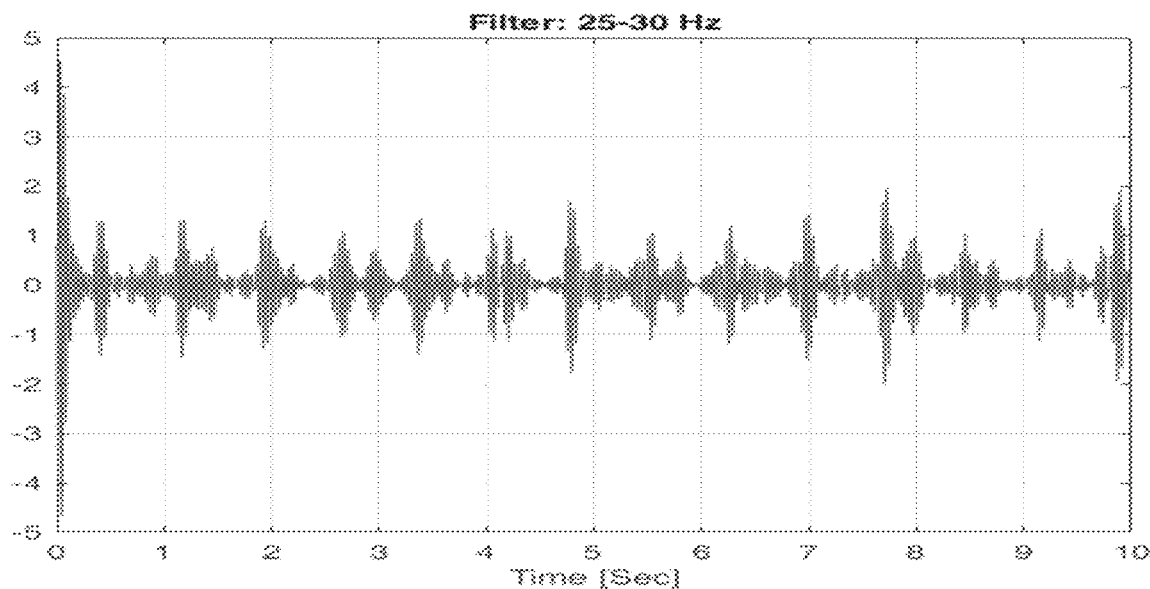
Figure 5F:
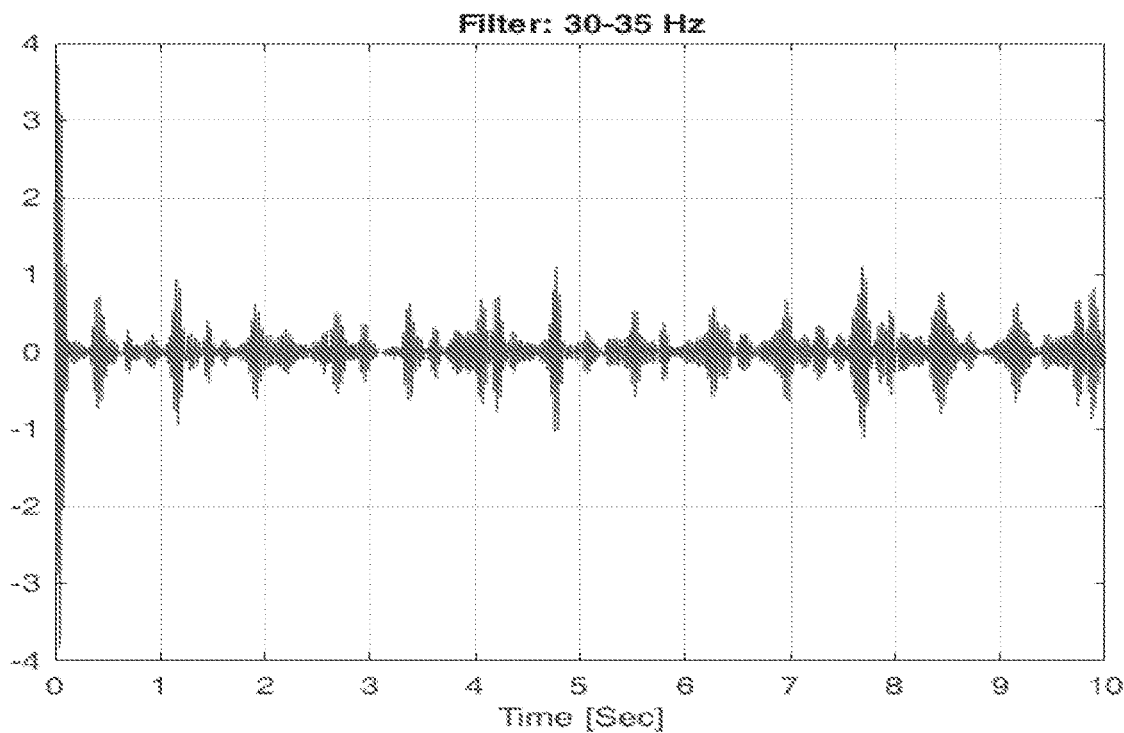
Figure 5G:
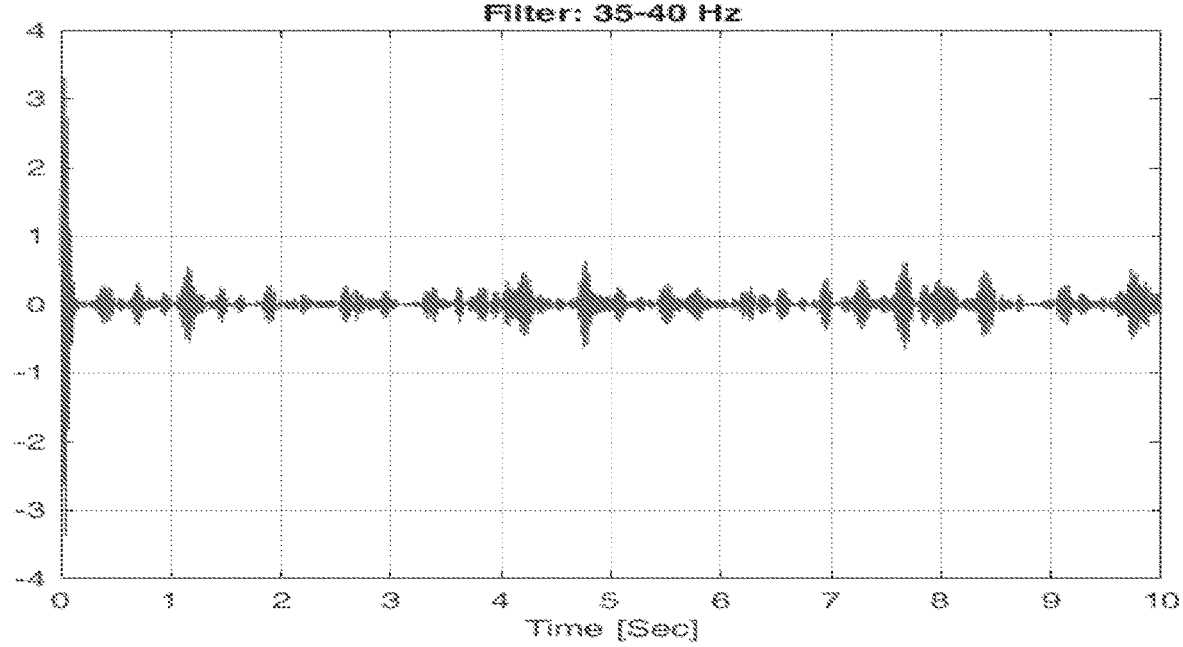
Figure 5H:
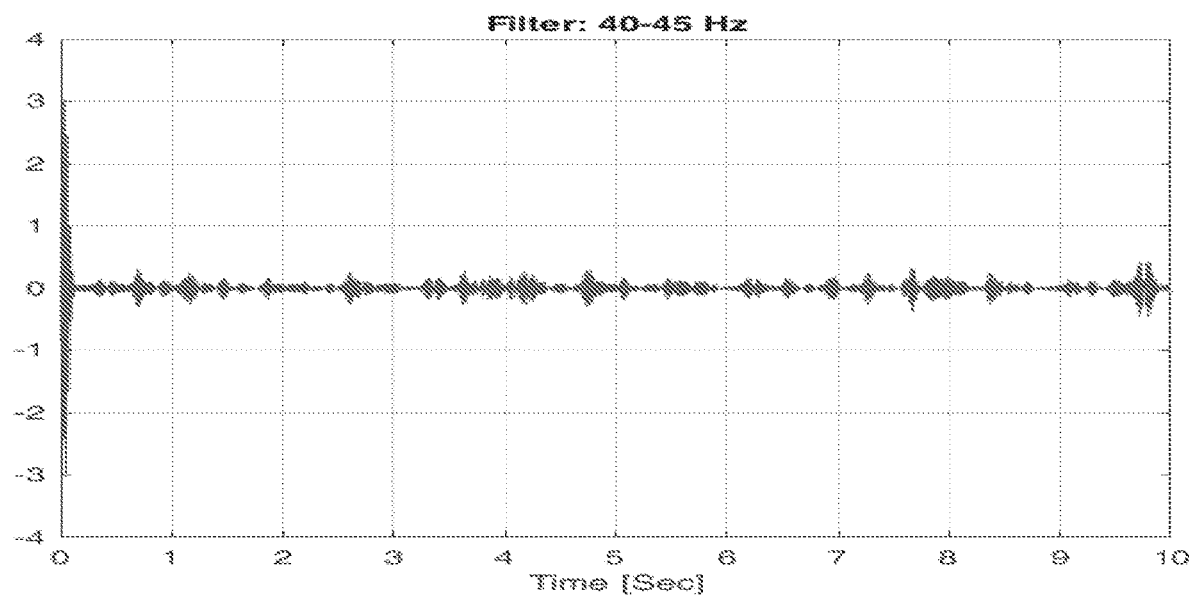

In some embodiments, as a first sub-step, the exemplary Div-Conq algorithm may be programmed to filter the T1 signal by utilizing one or more suitable digital filters to output further transformed signal data (T2 signal data). For example, one type of suitable filters may be, but not limited to, Butterworth two-step bandpass filters (high/low pass, 6th order), having narrow bandwidth to be set at 5 Hz, lowest frequency limit to be set at 5 Hz, and highest frequency limit to be set at 100 Hz. FIG. 4 illustrates an exemplary magnitude response of the exemplary digital filter that may be utilized for the sub-step 1.

FIGS. 5A-5H show examples of passbands of maternal PCG signal filtered with different filters.

Figure 6A:
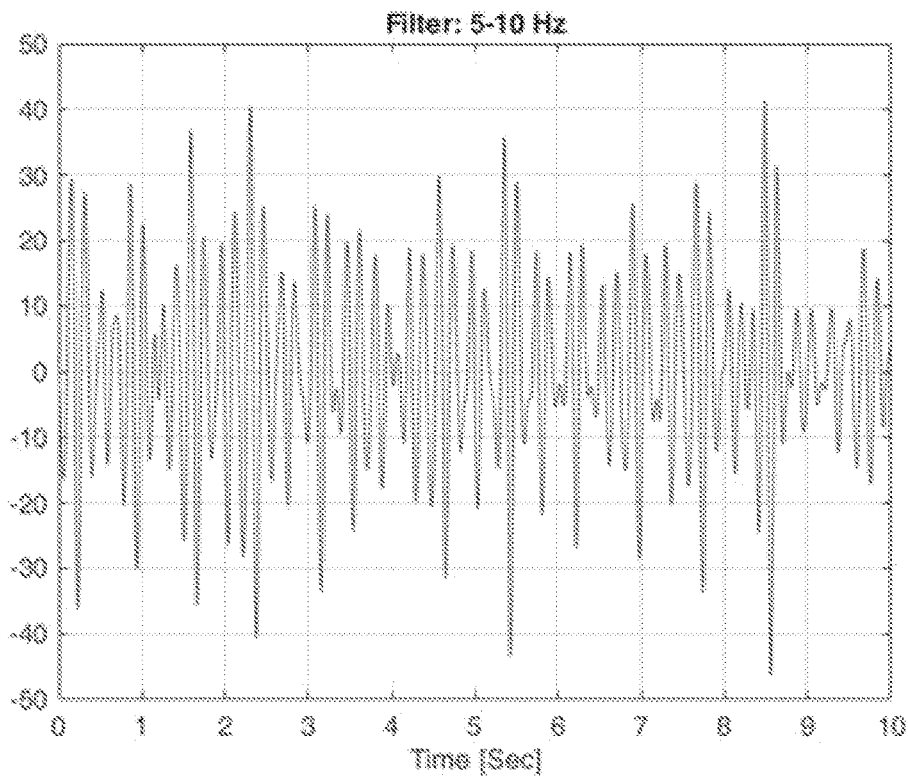
FIGS. 6A-6W show examples of passbands of T2 signals from different filters having various bandwidths, where the inputted 10 second time intervals of T1 signals have both maternal and fetal PCG signals.
Figure 6B:
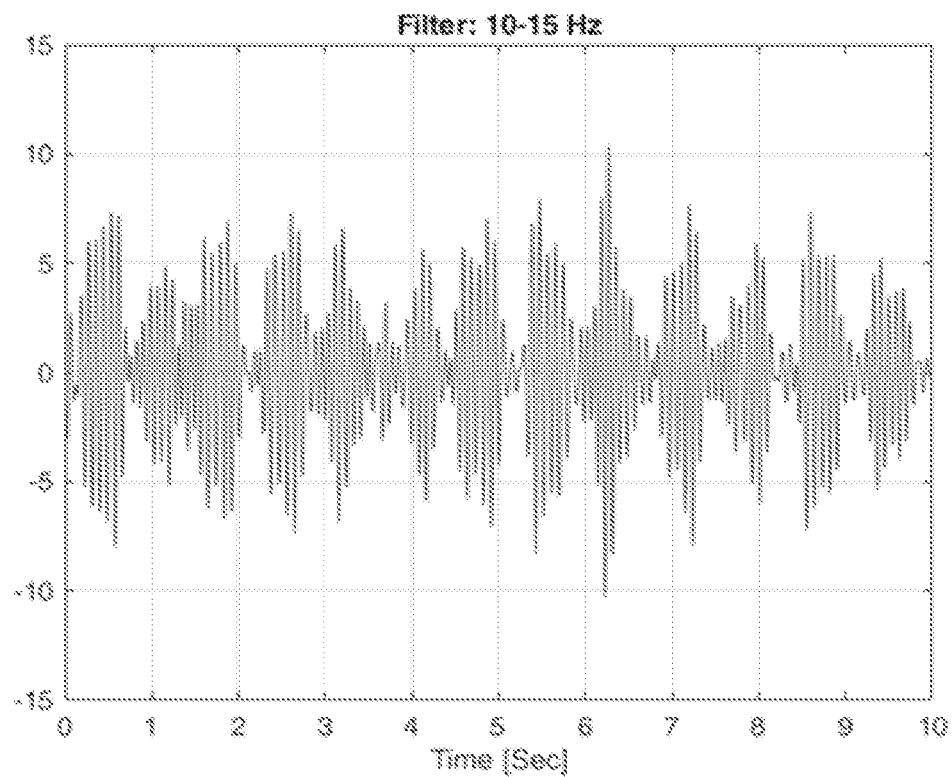
Figure 6C:
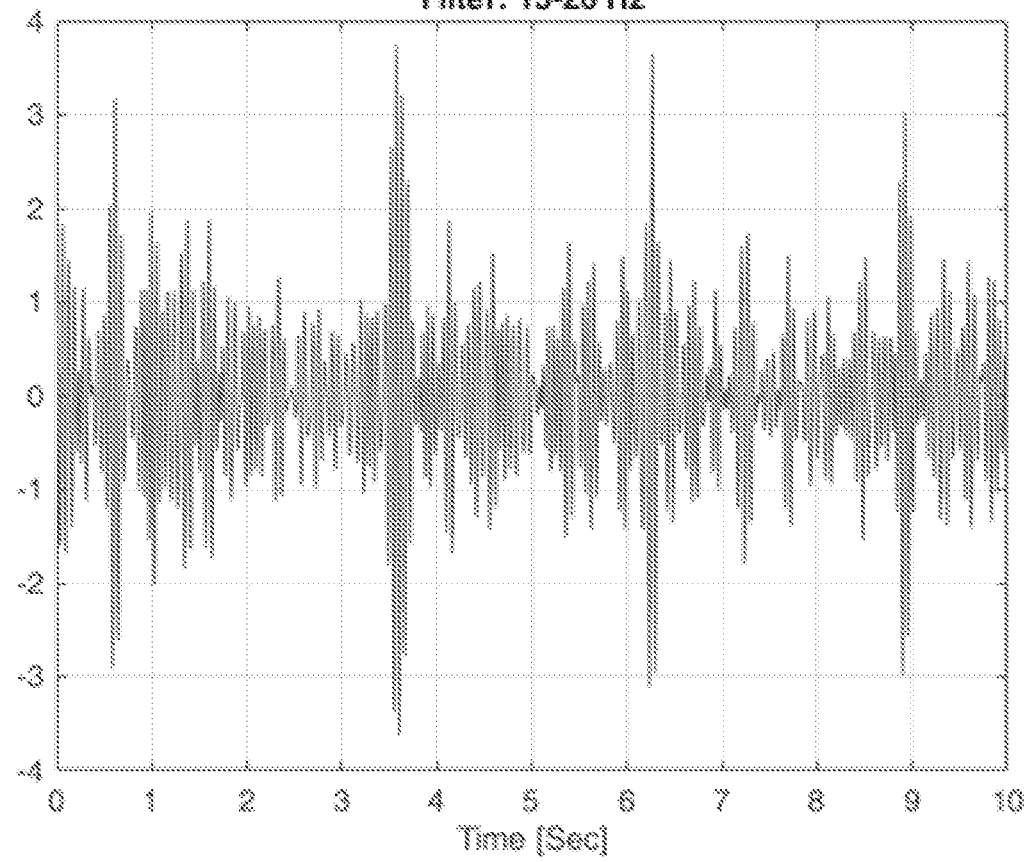
Figure 6D:
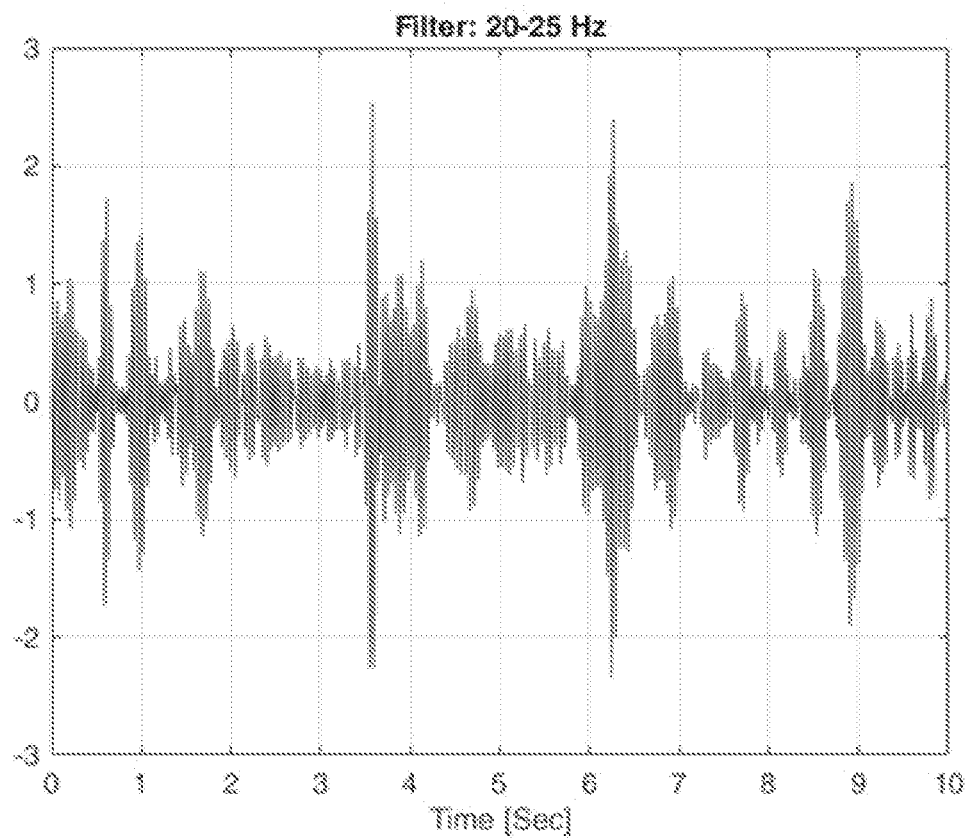
Figure 6E:
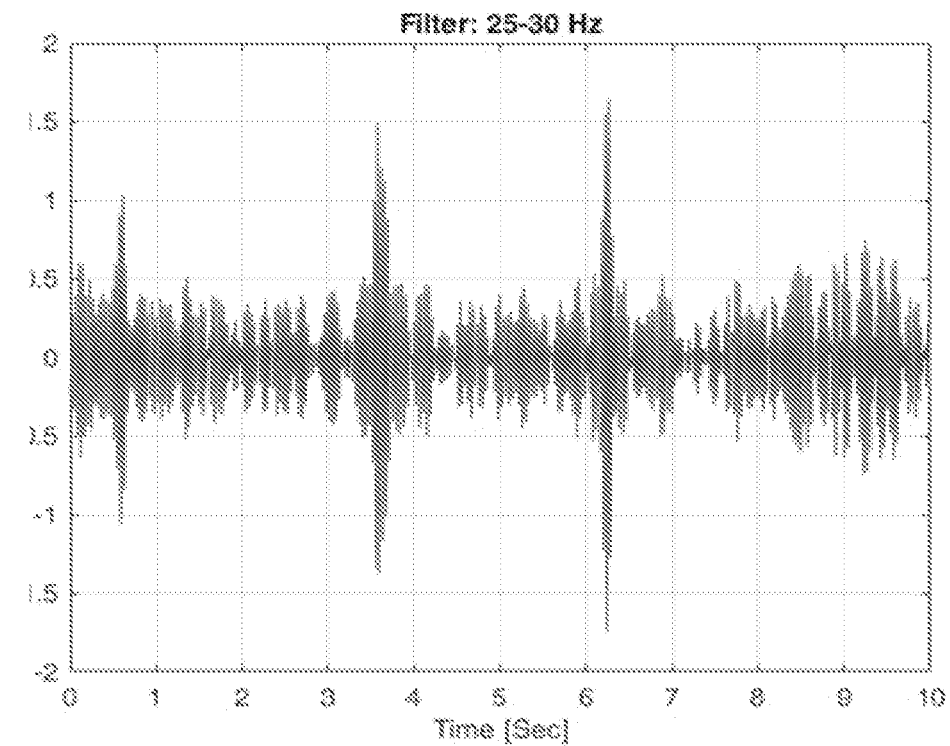
Figure 6F:
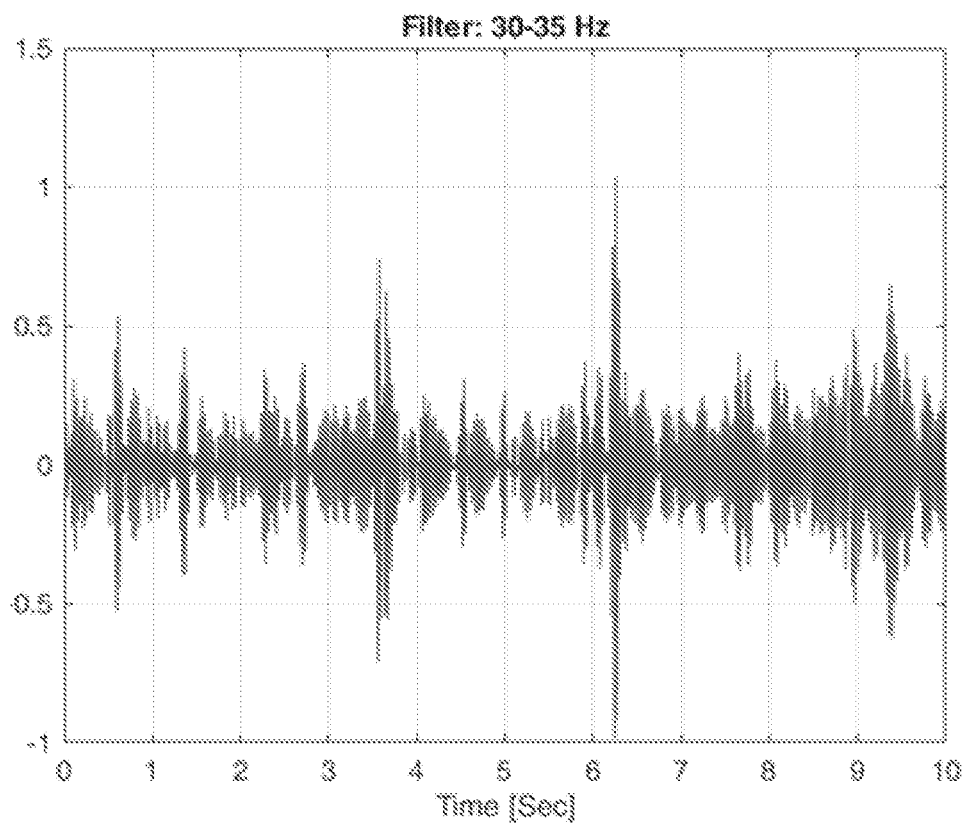
Figure 6G:
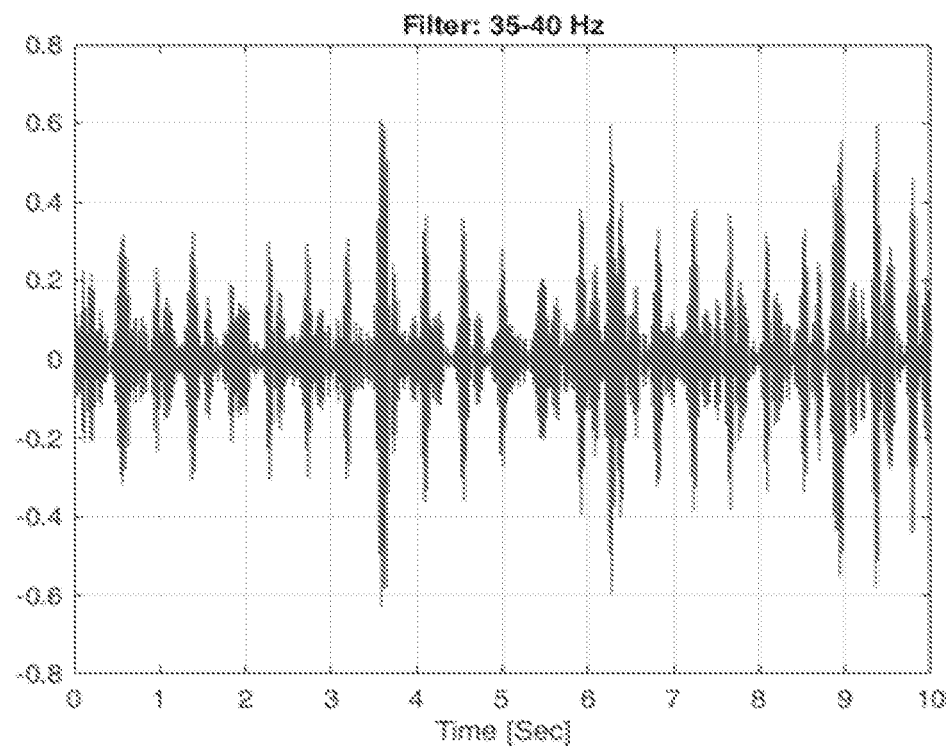
Figure 6H:
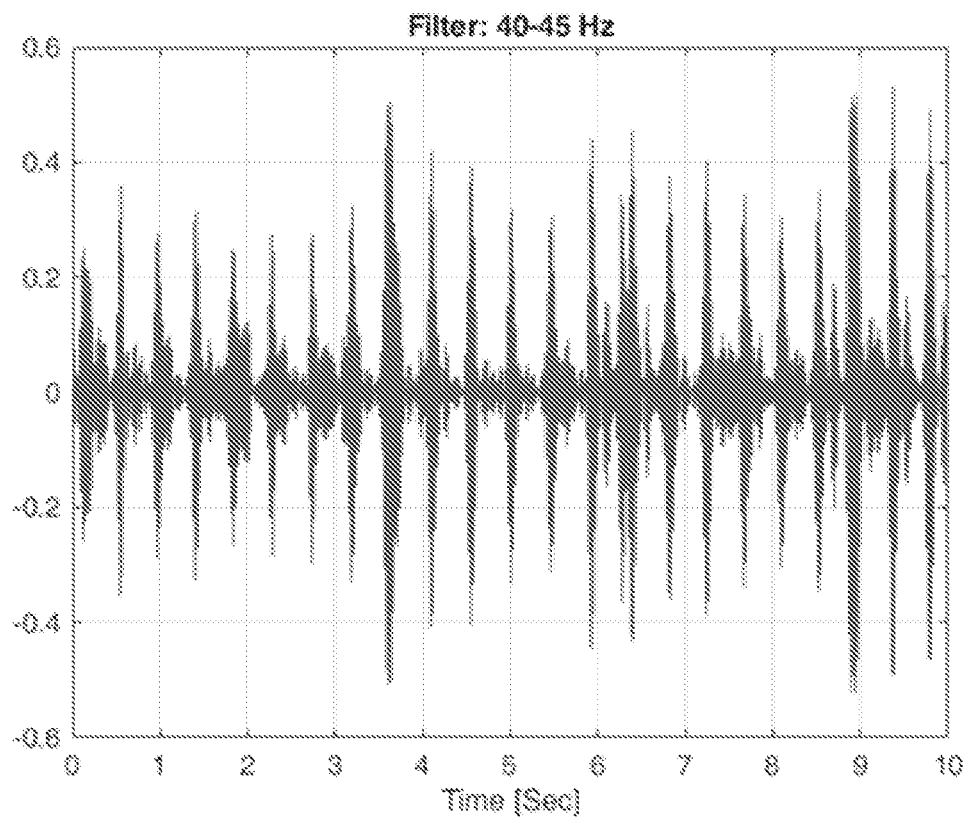
Figure 6I:
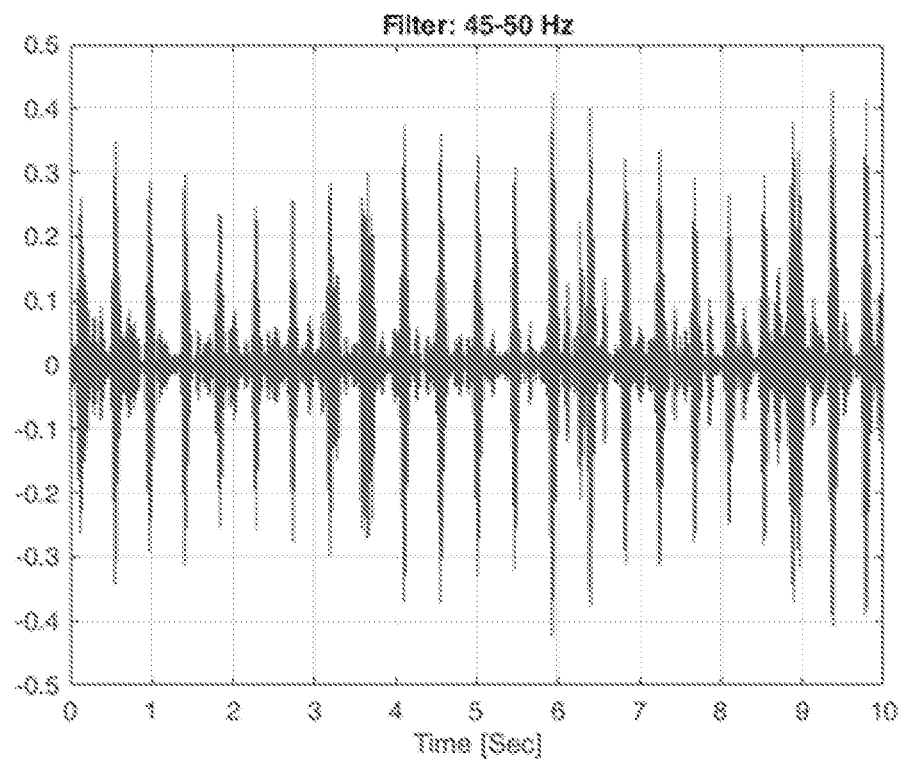
Figure 6J:
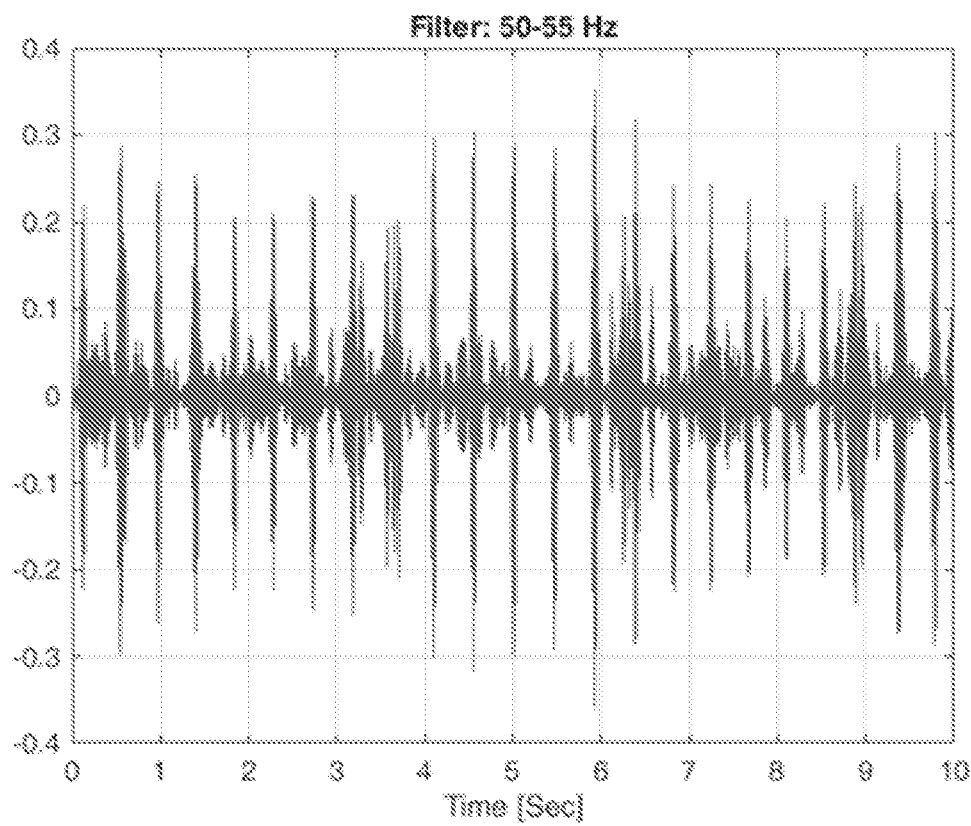
Figure 6K:
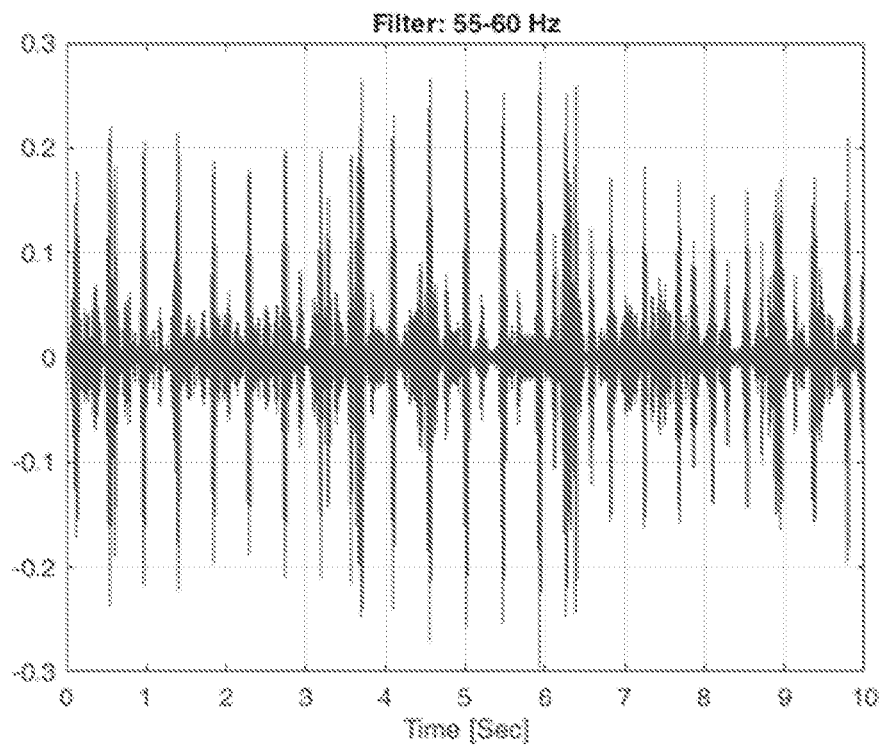
Figure 6L:
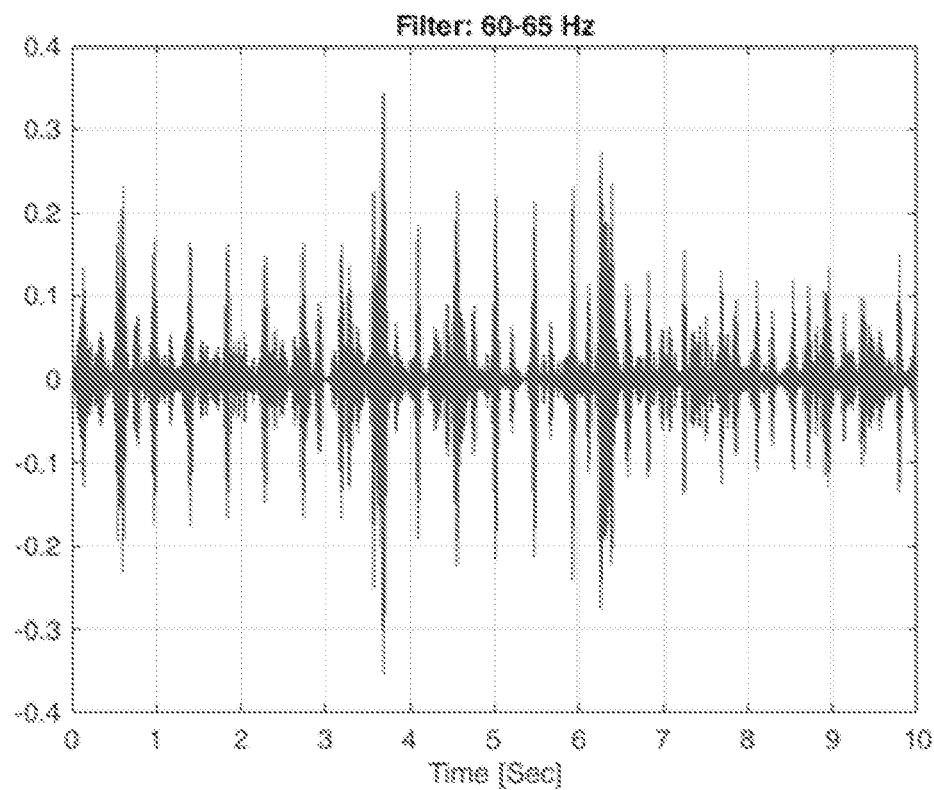
Figure 6M:
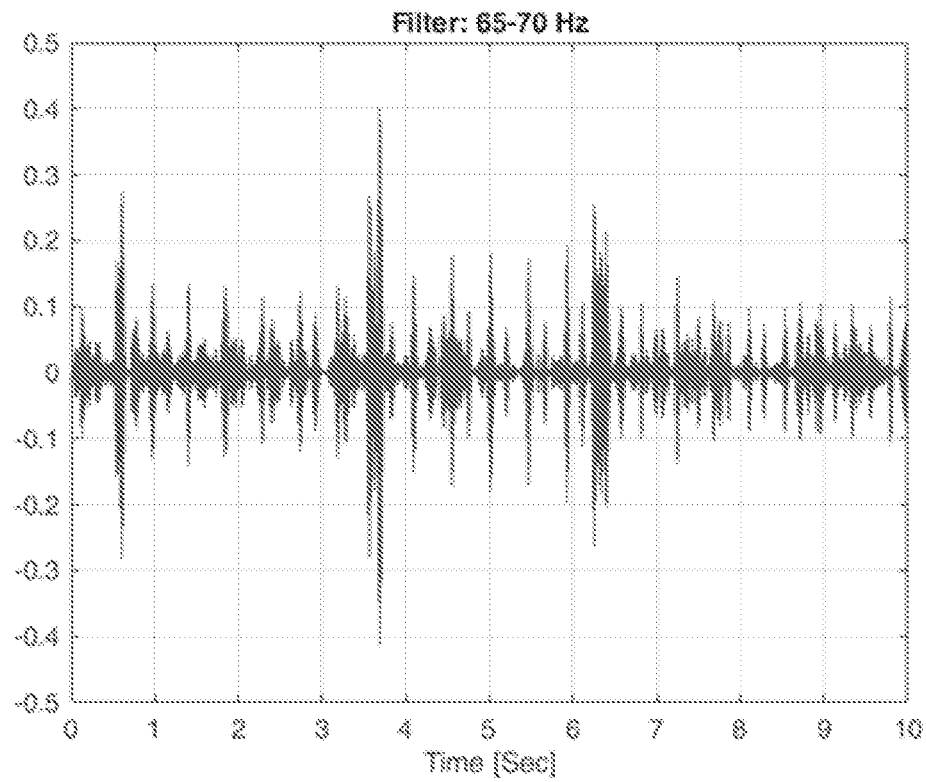
Figure 6N:
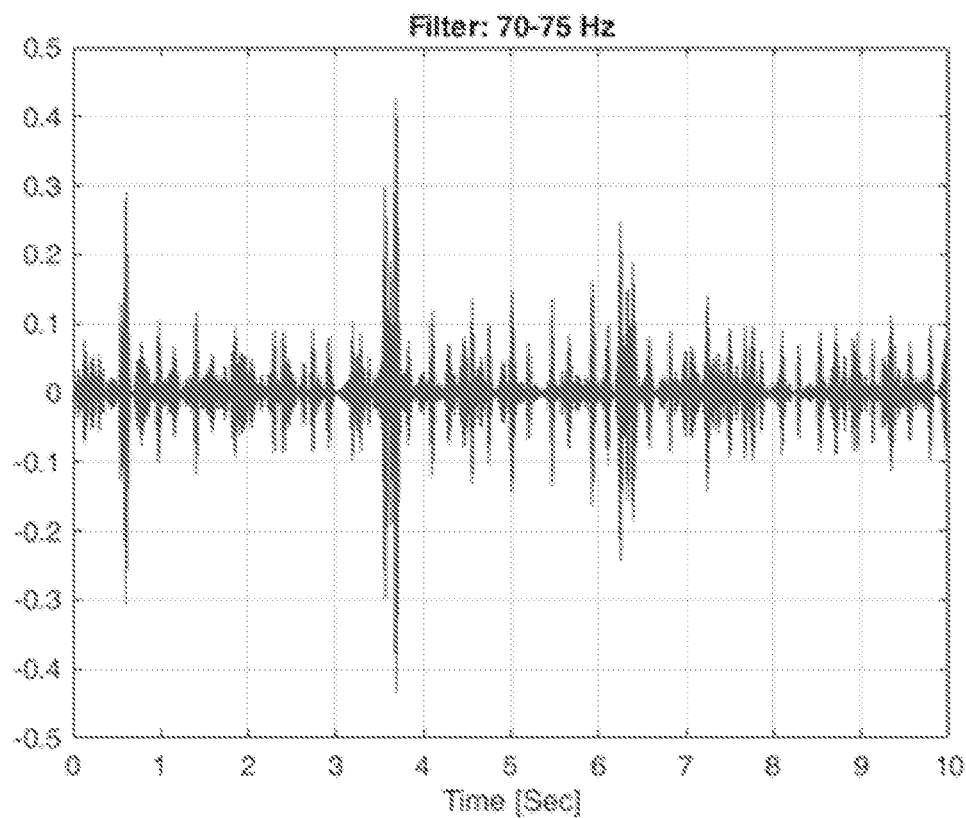
Figure 6O:
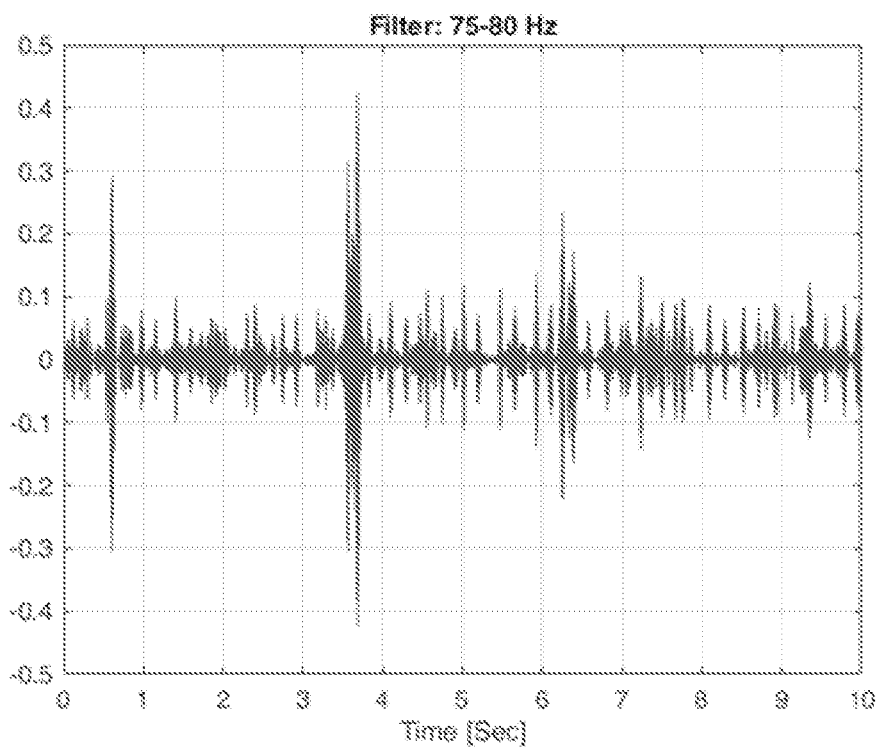
Figure 6P:
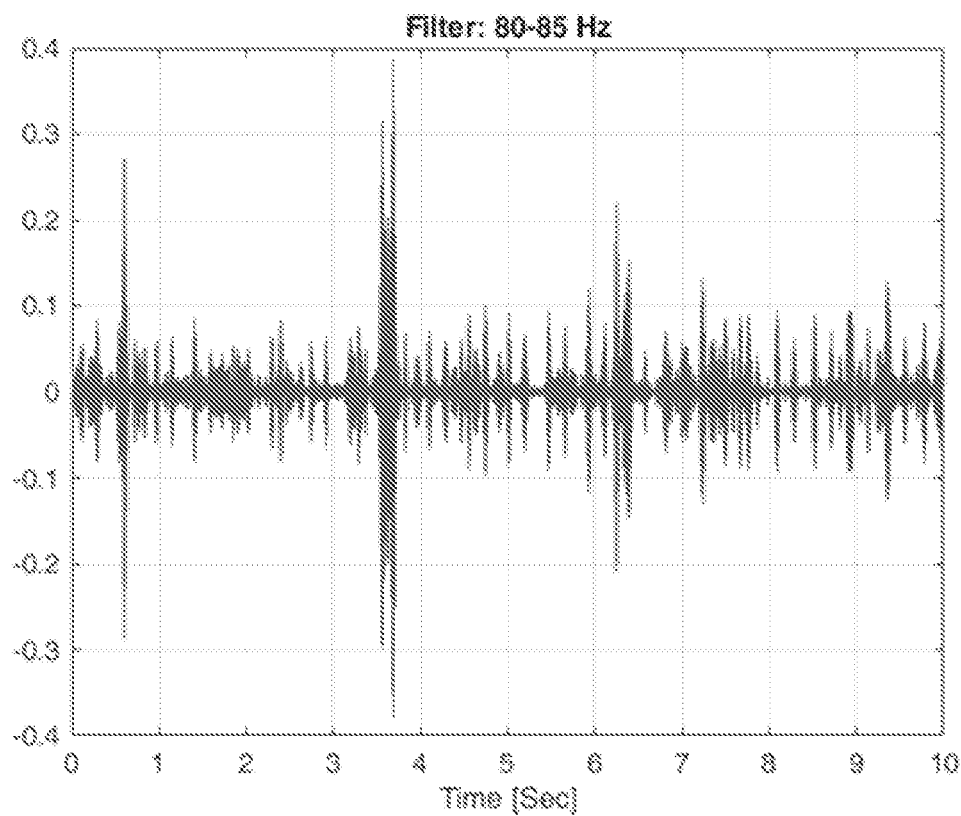
Figure 6Q:
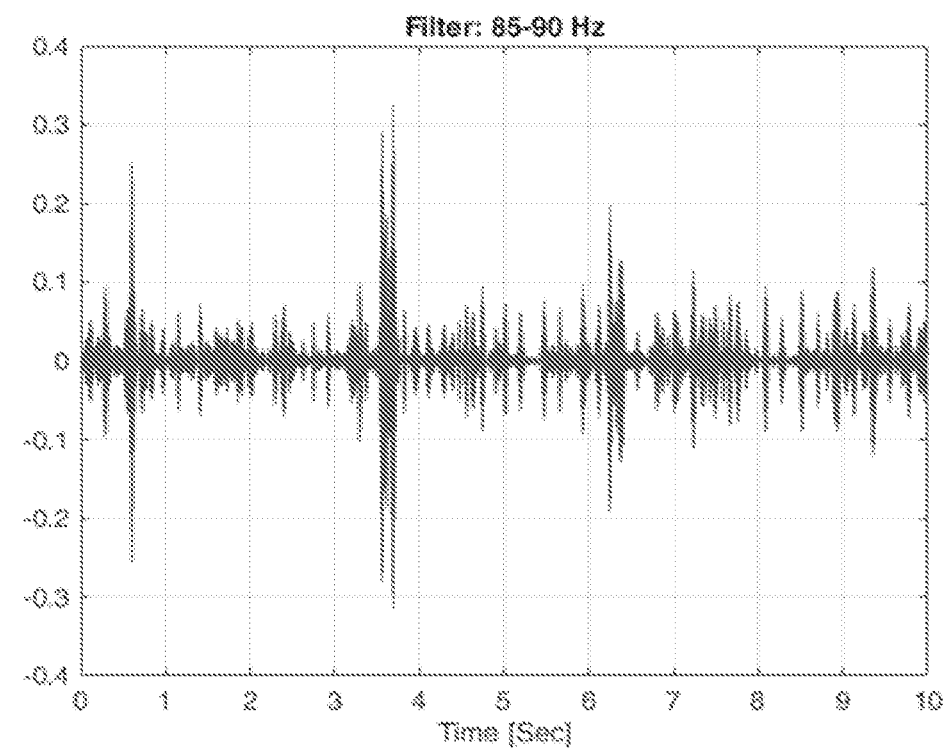
Figure 6R:
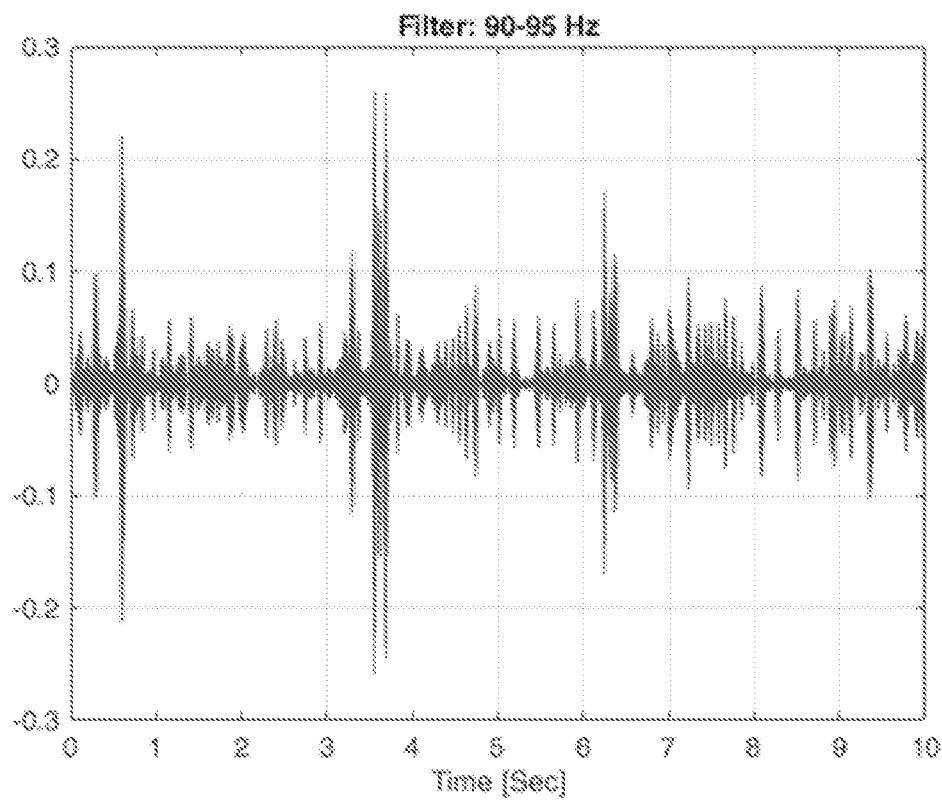
Figure 6S:
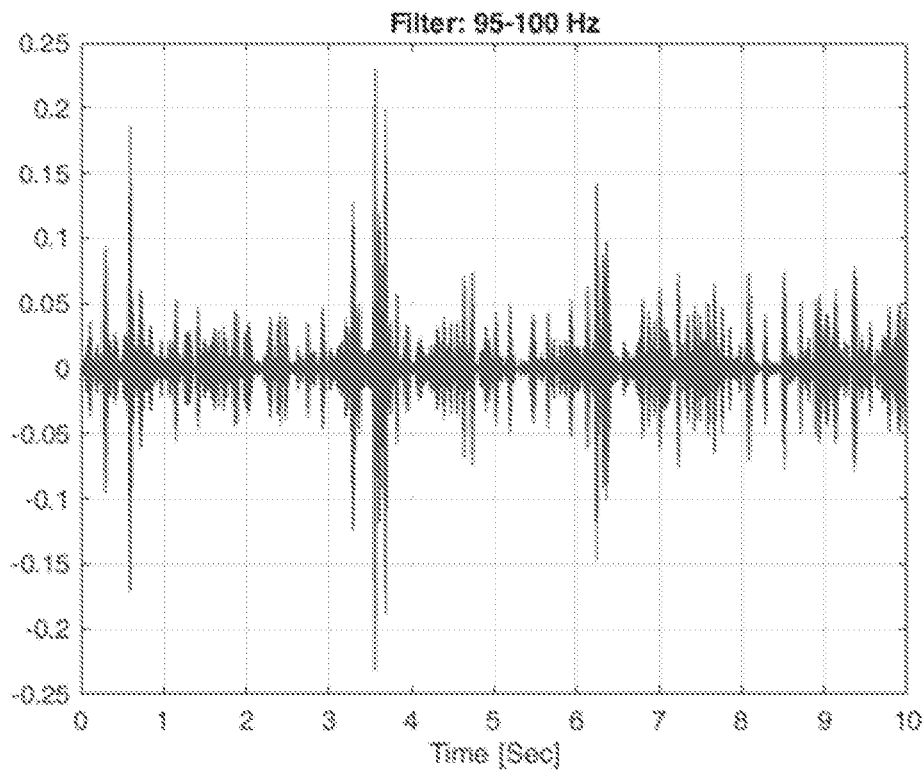
Figure 6T:
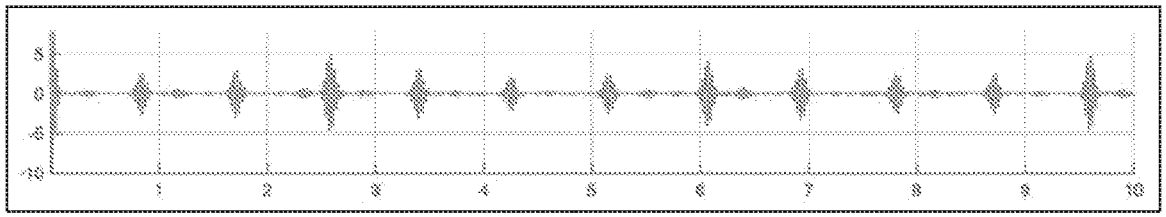
Figure 6U:
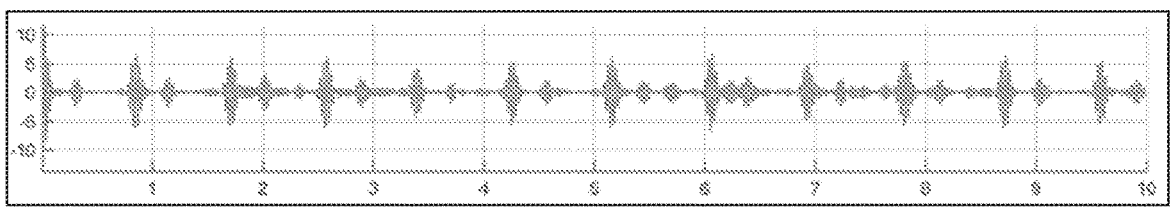
Figure 6V:
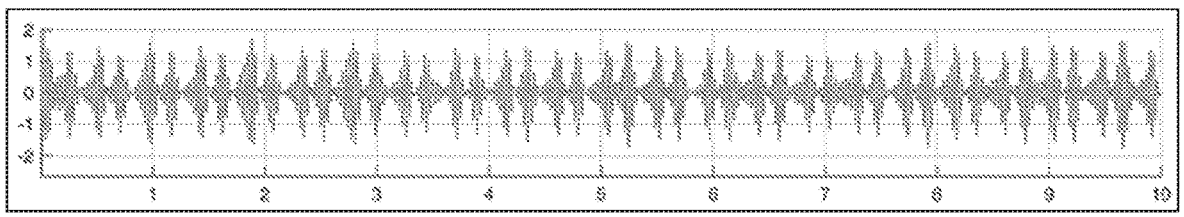
Figure 6W:
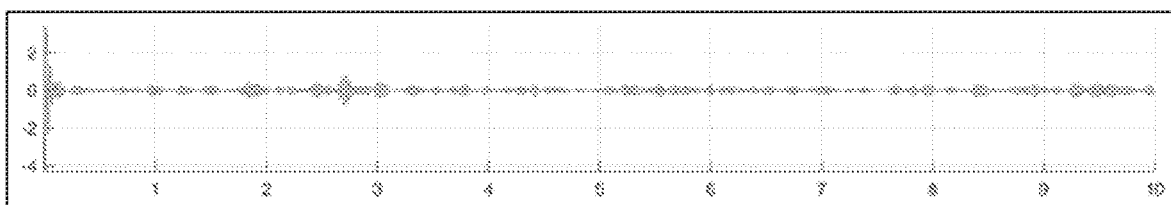

FIGS. 6A-6W show examples of passbands of T2 signals from different filters having various bandwidths, where the inputted 10 second time intervals of T1 signals have both maternal and fetal PCG signals.

Sub-Step 2

In some embodiments, as a second sub-step, the exemplary Div-Conq algorithm may be programmed to perform equalization of the T2 signal data based, at least in part, on energy distribution (e.g., RMS window) among frequency bands.

Sub-Step 3

In some embodiments, as a third sub-step, the exemplary Div-Conq algorithm may be programmed to enhance peaks in the T2 signal data based, at least in part, on a distance from the mean of the signal (Mean Absolute Deviation (MAD) window)

Figure 7:
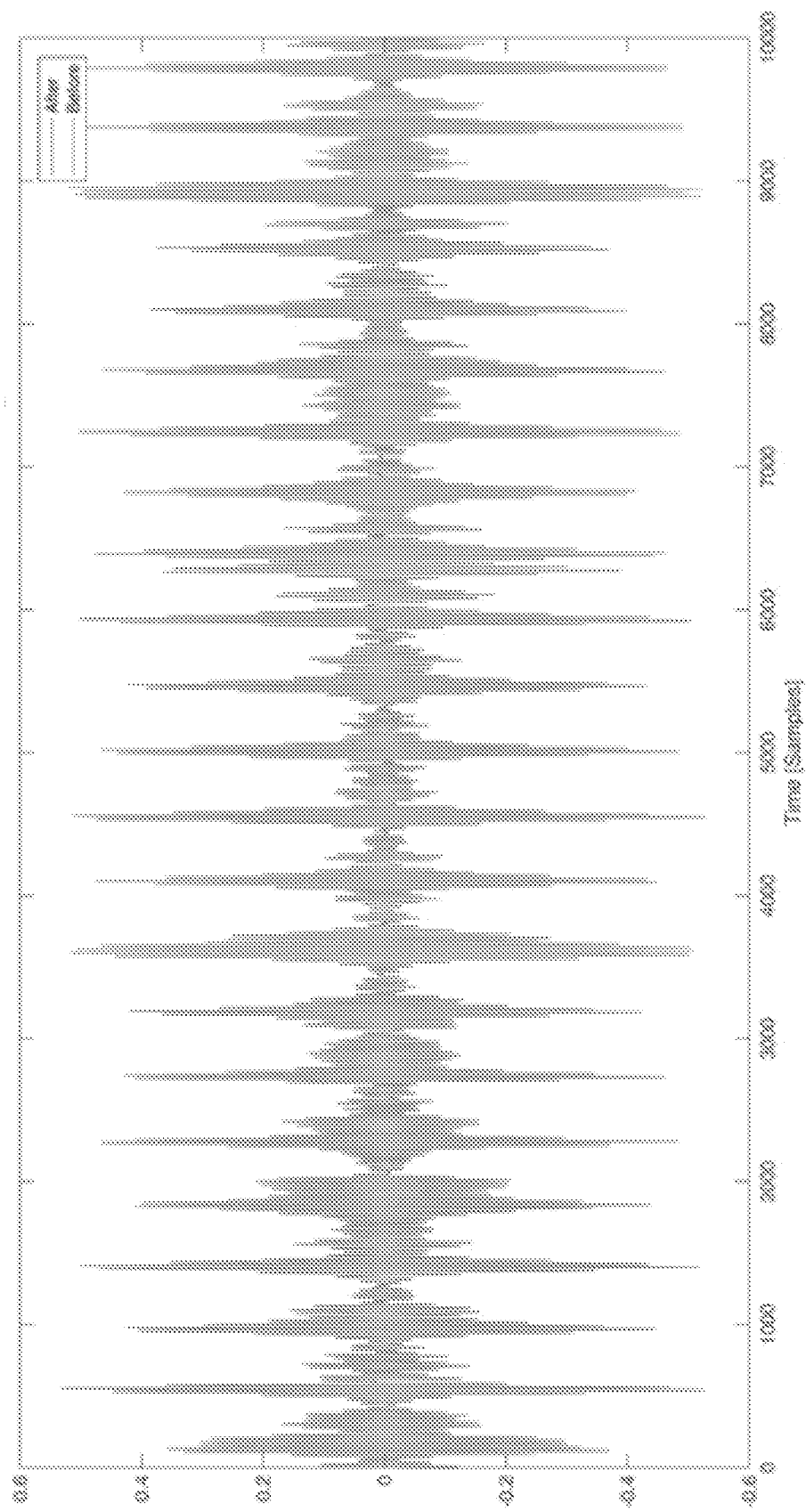
FIG. 7 shows states of T2 signal data before and after the performance of sub steps 2 and 3.

FIG. 7 shows states of T2 signal data before and after the performance of sub steps 2 and 3.

Figure 8A:
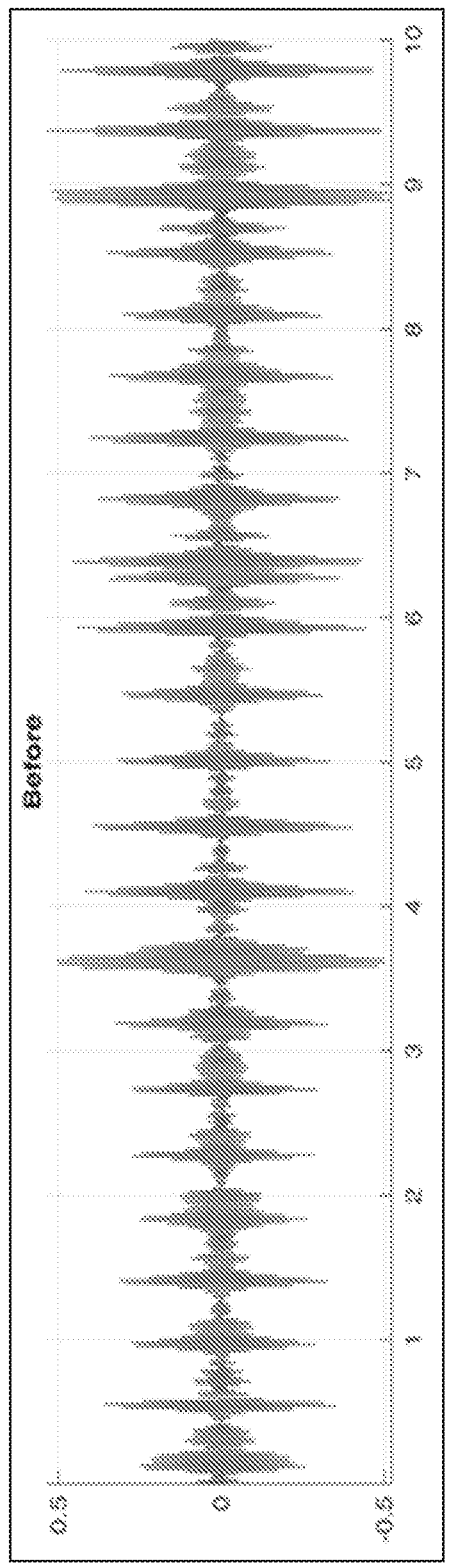
FIG. 8A shows a state of T2 signal data before the performance of sub-steps 2 and 3.

FIG. 8A shows a state of T2 signal data before the performance of sub-steps 2 and 3.

Figure 8B:
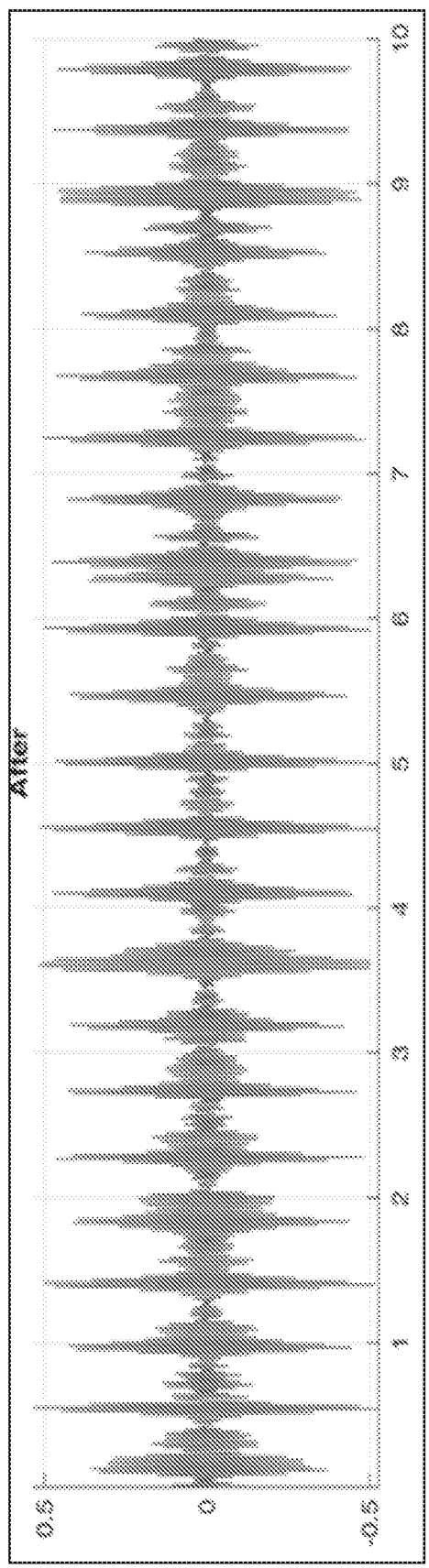
FIG. 8B shows a state of T2 signal data after the performance of sub-steps 2 and 3.

FIG. 8B shows a state of T2 signal data after the performance of sub-steps 2 and 3.

Sub-Step 4

Figure 9:
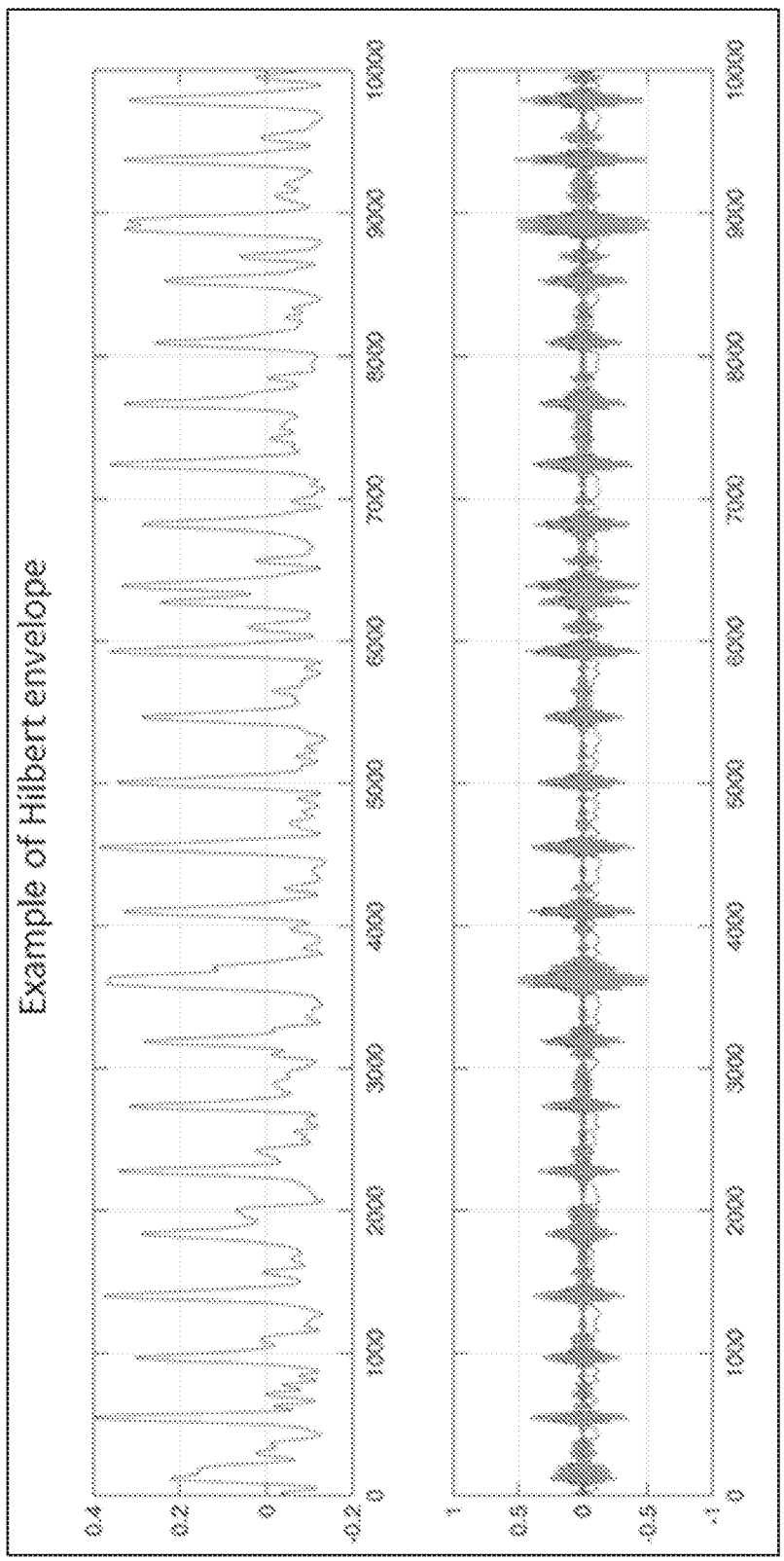
FIG. 9 shows an example of Hilbert envelope in T3 signal data.

In some embodiments, as a fourth sub-step, the exemplary Div-Conq algorithm may be programmed to subject T2 signal data to a complex Hilbert transform filter to obtain T3 signal data. In some embodiments, the exemplary Hilbert transform filter may be based on a low-pass filter such as, but not limited to, a $5^{th}$ order Butterworth low-pass filter having a cutoff frequency of 20 Hz. T3 signal data then further centered around zero. FIG. 9 shows an example of Hilbert envelope in T3 signal data.

Sub-Step 5

In some embodiments, as a fifth sub-step, the exemplary Div-Conq algorithm may be programmed to take a valid channels of T3 signal data (e.g., by utilizing, for example, the binary SVM classifier as detailed above) and detect compartments, where compartments may be, but not limited to, S1, the first heart sound (lup) which occurs on closure of AV valves, and S2, the second hear sound which occurs on the closure of semilunar valves. In some embodiments, the detection may recognize any compartments whether they are maternal or fetal origin. In some embodiments, the exemplary Div-Conq algorithm may be programmed to detect compartments by utilizing, for example, without limitation, at least a partial auto correlation function to measure a similarity between a signal and its time delayed version. For example, the exemplary Div-Conq algorithm may be programmed to apply the partial auto correlation as a correlation between a time series and its lags with the effects of lower order lags held constant so that to further remove the linear ties between the lagged series. For example, the partial autocorrelation function (PACF) may be calculated using the Durbin-Levinson algorithm. For example, after calculating the full auto correlation, the exemplary Div-Conq algorithm may be programmed to select a half of results. For example, if the length of the auto correlation array would be 10000, the exemplary Div-Conq algorithm may be programmed to select 5000 elements. In such case, the exemplary Div-Conq algorithm may be programmed to select the second half: from the 5001st element until the 10000th element.

Figure 10:
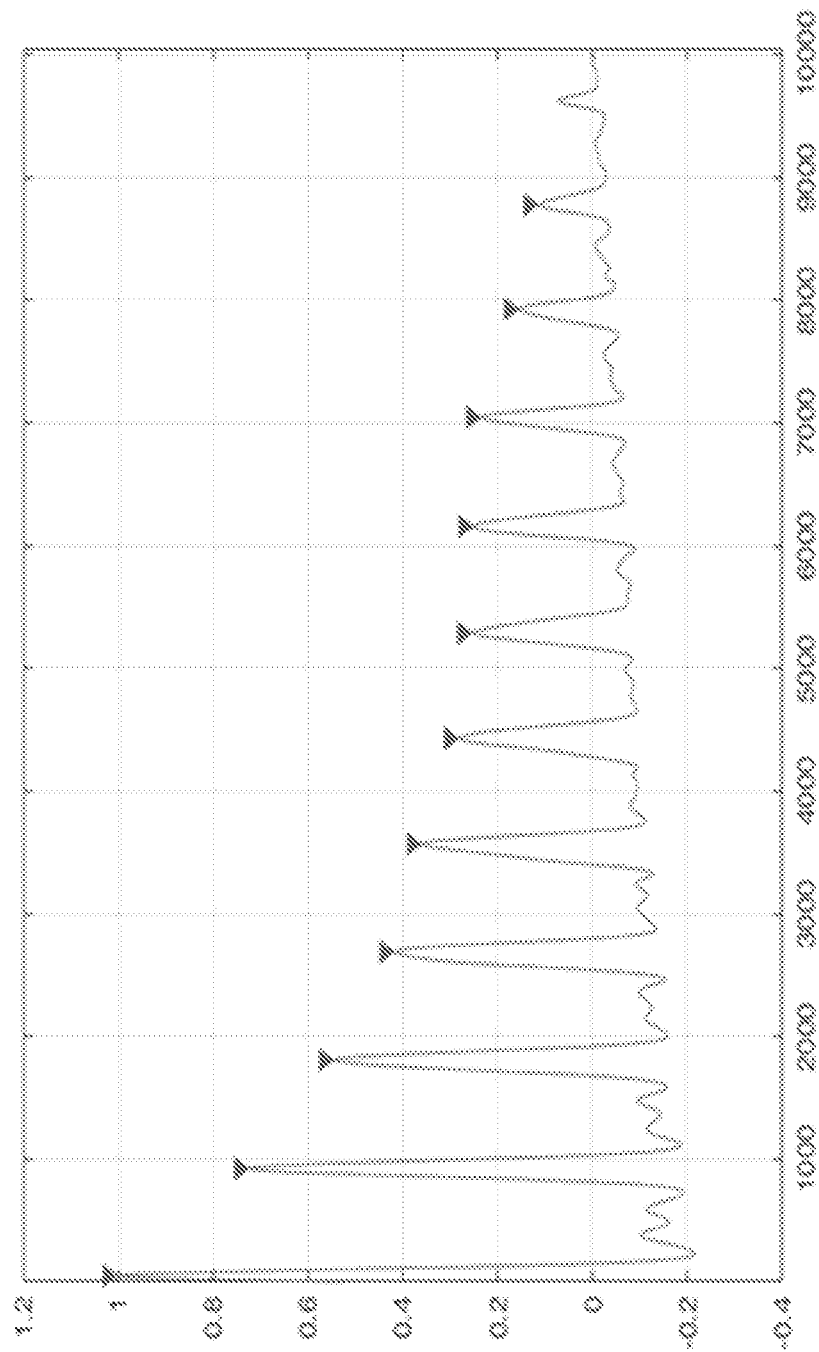
FIG. 10 shows an example of applying an auto correlation function in a case of a single compartment.

FIG. 10 shows an example of applying an auto correlation function in a case of a single compartment.

Figure 11:
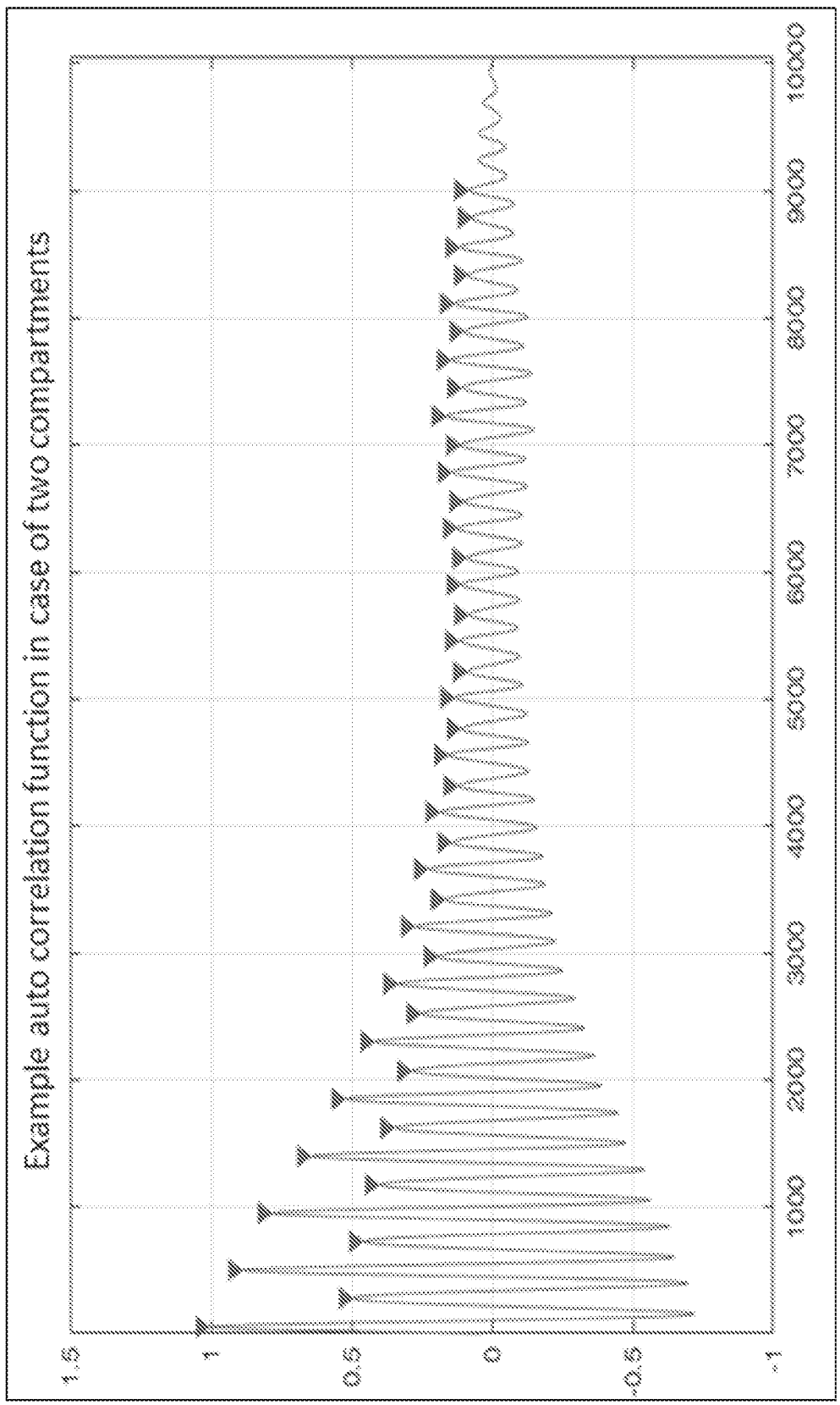
FIG. 11A shows peaks after applying the auto correlation function to T3 signal data.
FIG. 11B shows a difference signal of FIG. 11A with normalization.
FIG. 11C shows an output based on a distance to closest value.

FIG. 11A shows peaks after applying the auto correlation function to T3 signal data. FIG. 11B shows a difference signal of FIG. 11A with normalization. FIG. 11C shows an output based on a distance to closest value.

Figure 12A:
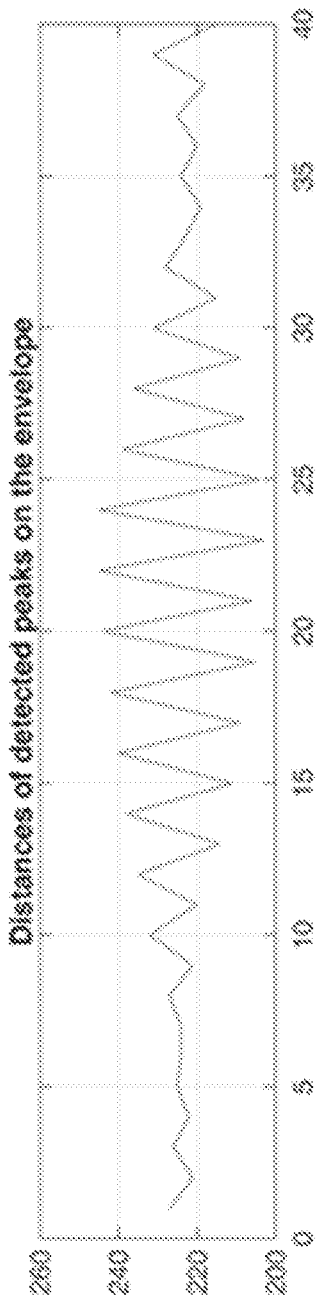
FIGS. 12A-12C show use of an envelope signal if a score is not acceptable.
Figure 12B:
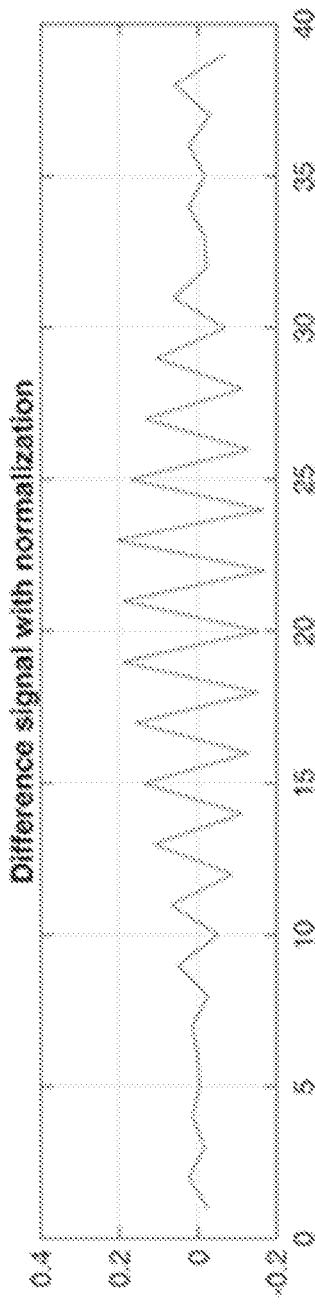
Figure 12C:
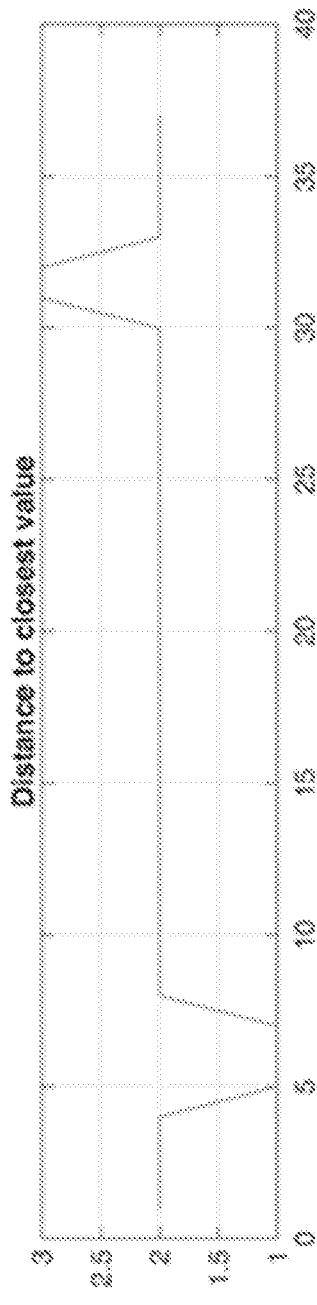

In some embodiments, if more than one group of compartments have been detected, the exemplary Div-Conq algorithm may be programmed to determine if groups could be or should be merged. In some embodiments, if more than one group of compartments have been detected, the exemplary Div-Conq algorithm may be programmed to test the groups by utilizing another suitable scoring technique, such as the MAD methodology described above. If a score is not acceptable (e.g., the score is higher than 50), the exemplary Div-Conq algorithm may be programmed to utilize the envelope signal itself, as shown in FIGS. 12A-12C.

In some embodiments, the exemplary Div-Conq algorithm may be programmed to detect compartments in the T3 signal by, but not limited to, (1) estimating beat-to-beat intervals and (2) determining whether compartments have originated in same signal (e.g., S1S2) or whether compartments have originated from different signals (i.e., maternal and fetal signals). In some embodiments, the origin testing can be performed by utilizing, without limitation, a cross correlation of impulse signals generated by each compartment and applying a dynamic time wrap function (DTW) that is an algorithm suitably configured for measuring similarity between at least two temporal sequences which may vary in time and/or speed. For example, an exemplary DTW may rely on dynamic programming (DP) to find a path that minimizes the total cost. For example with positive costs, finding both the low-cost cells and minimizing the total number of steps.

Case 0: 0 Signal, 0 Compartment

If no compartment has been found, stop processing with this filter (e.g., the 19 Butterworth two-step bandpass filter).

Case 1: 1 Signal, 1 Compartment

Identify peak(s) in the T3 signal data based, at least in part, on one of:

1) calculating:
   i) root-mean-square (RMS) envelope which may be calculated using a moving window, with each window of data calculated according to the following equation:

$$RMS = \left(\frac{1}{S}\Sigma_1^S f^2(S)\right)^{\frac{1}{2}}, \quad \text{(eq. 1)}$$

where S equals the window length (points) and f(s) equals the data within the window; and ii) multiplication of the RMS envelope of the Hilbert envelope.

Case 2: 1 signal, 2 Compartments

Figure 13:
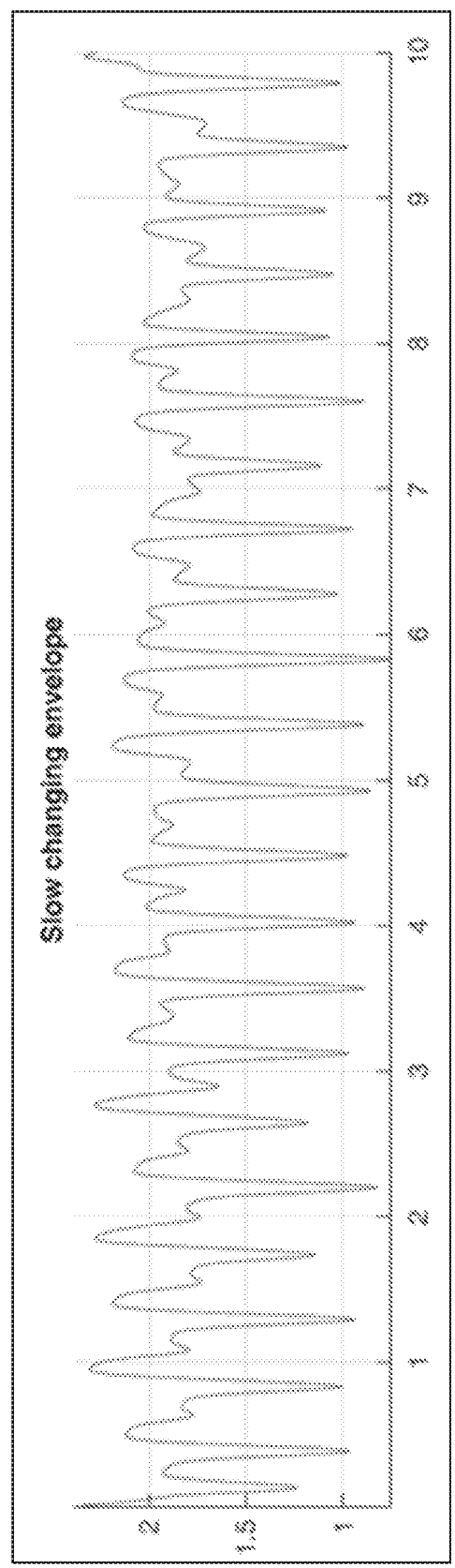
FIG. 13 shows calculation of a slow RMS envelope signal.
Figure 14:
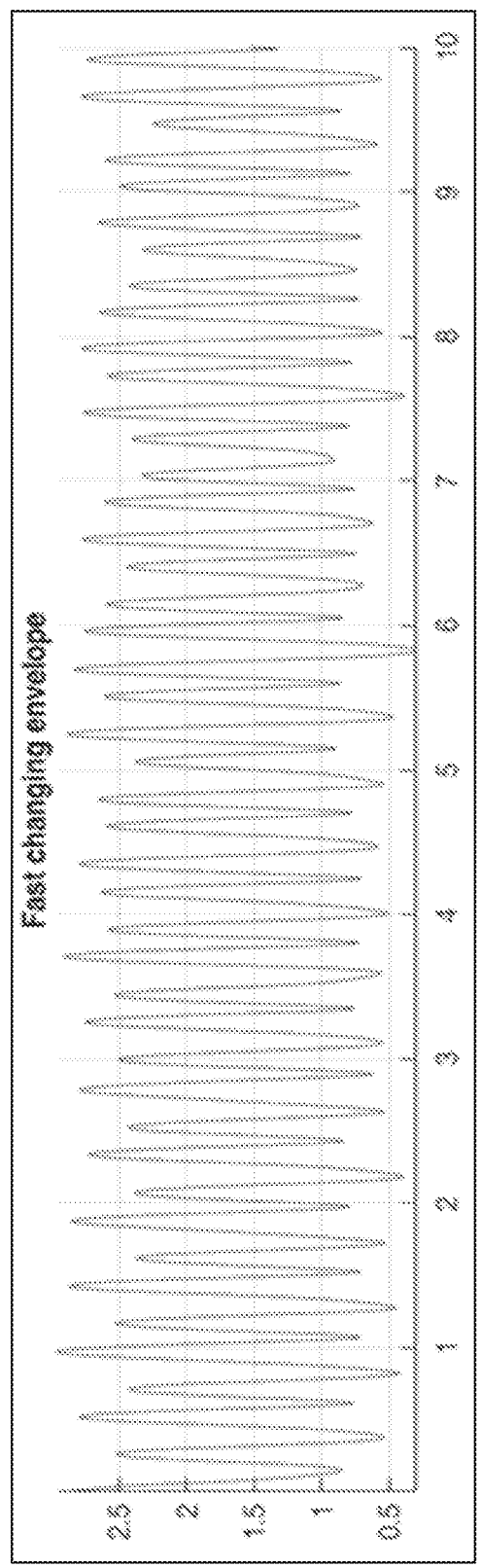
FIG. 14 shows calculation of a fast RMS envelope signal.

Identify pairs of peaks based, at least in part, on one of:

1) calculating a slow RMS envelope signal (window length=$\frac{2}{5}$ from the calculated average beat-2-beat interval) as, for example, shown in FIG. 13; and 2) calculating a fast RMS envelope signal (window length=$\frac{1}{5}$ from the calculated average beat-2-beat interval) as, for example, shown in FIG. 14.

Case 2: 1 signal, 2 Compartments

Identify pairs of peaks based, at least in part, on the fast envelope: find all peaks and to cluster peaks depending on the distances, by, for example:

i) estimating S1S2 and S2S1 durations;

ii) calculating the duration (width) of the S1/S2 complex; and iii) repeating validations (tuned for accuracy) (e.g., utilizing MAD approach detailed above).

For example, the peak clustering can be programmed so that:

i) a cluster of peaks to appear first is S1, and ii) a cluster of peaks to appear second is S2.

Figure 15:
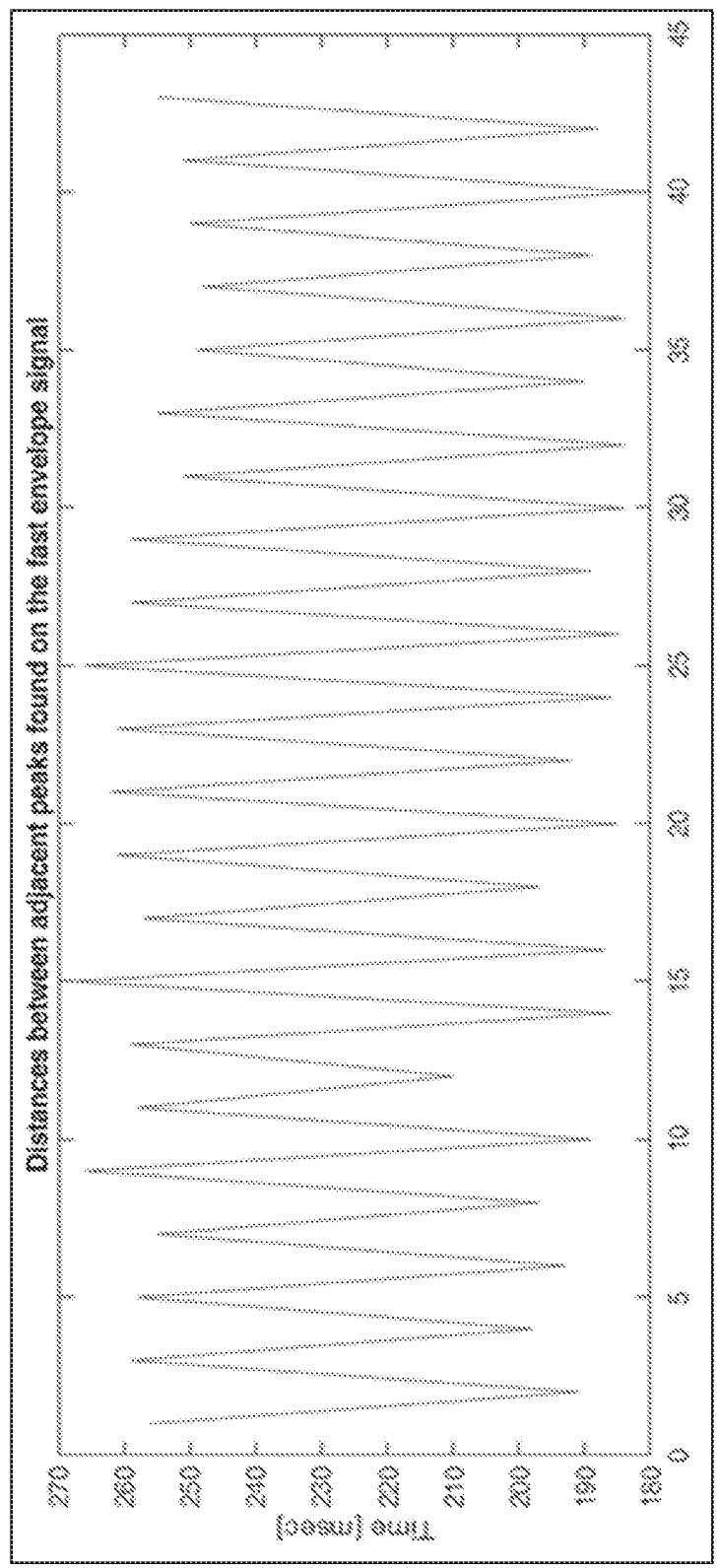
FIG. 15 shows determining peak-to-peak distances.
Figure 16:
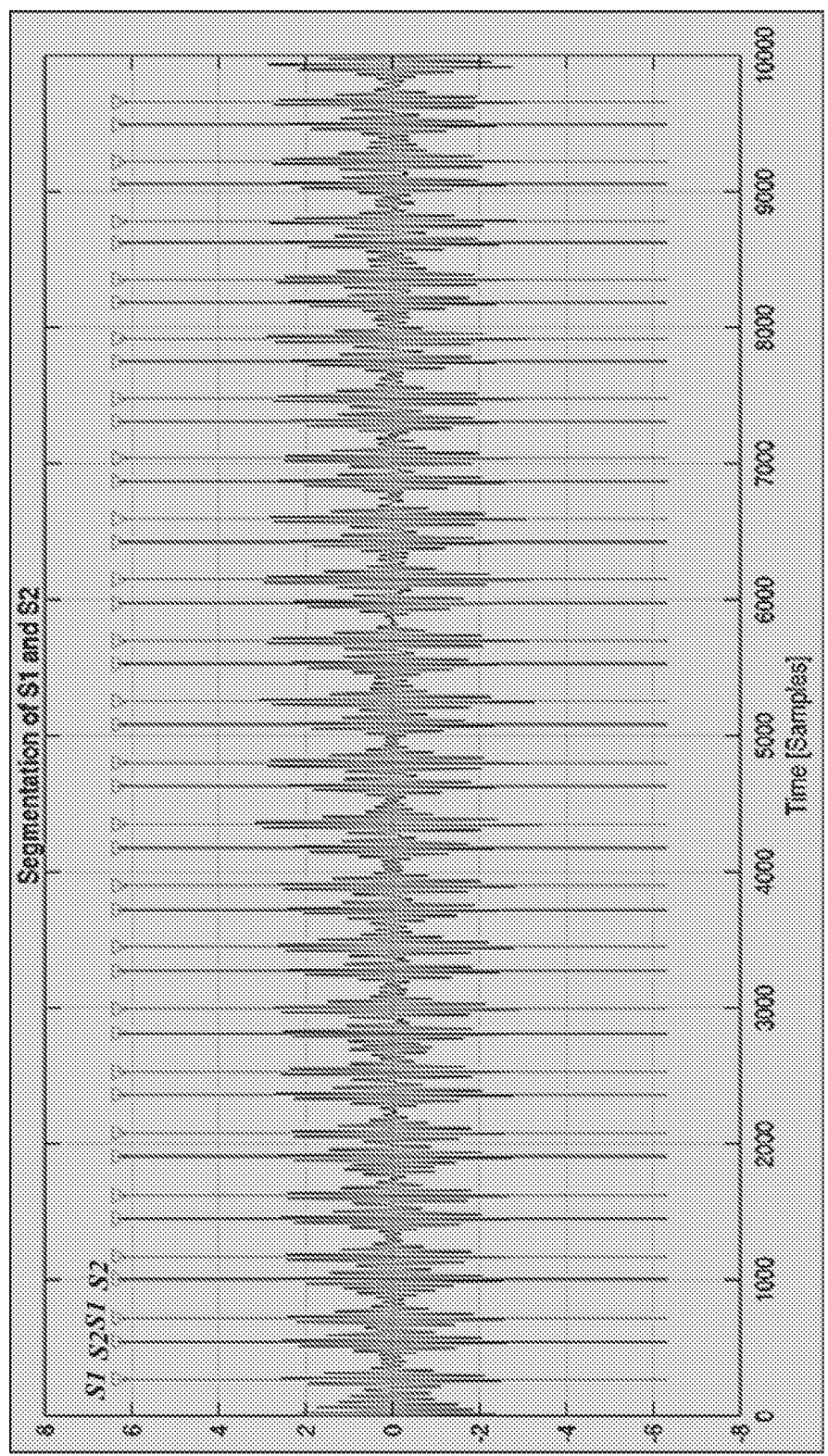
FIG. 16 shows clustering of S1 and S2 peaks.

For example, FIG. 15 shows determining peak-to-peak distances. For example, FIG. 16 shows clustering of S1 and S2 peaks.

Figure 17:
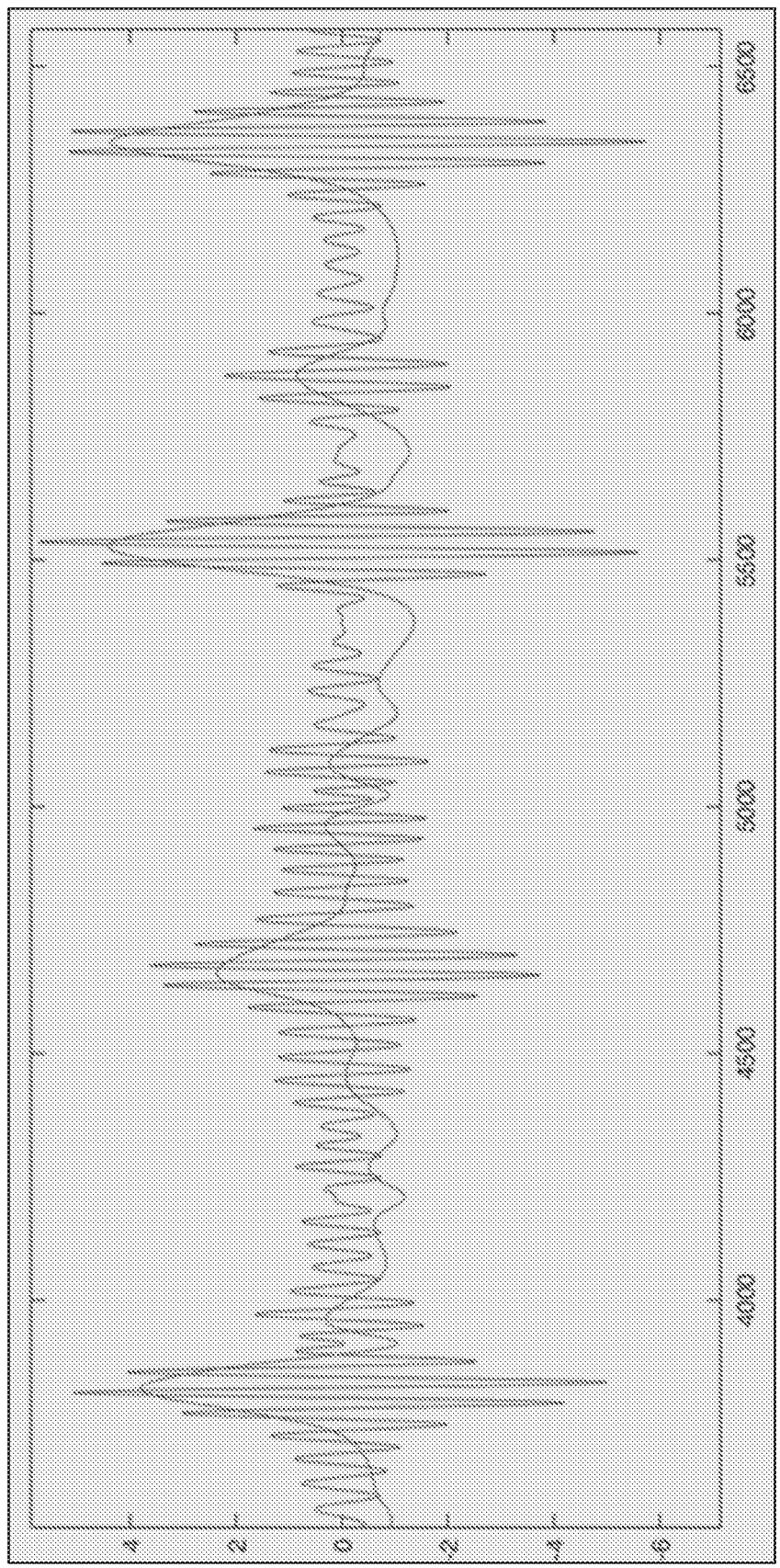
FIG. 17 shows that heart sounds are typically skewed because of noises.
Figure 18:
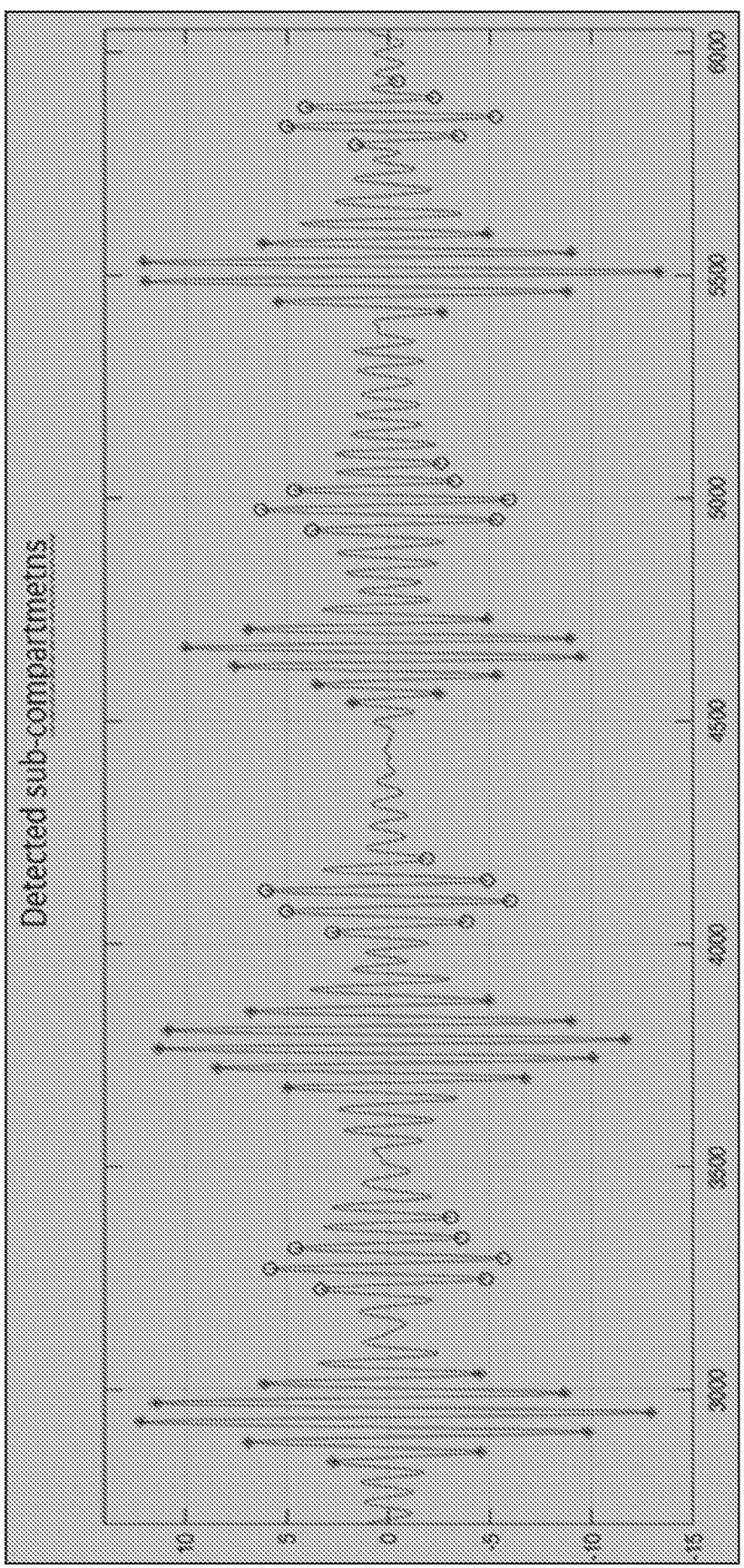
FIG. 18 shows sub-compartments within heartbeats.

FIG. 17 shows that heart sounds are typically usually skewed because of noises. Consequently, the exemplary Div-Conq algorithm may be programmed to detect each compartment by:

i) identifying related beats;

ii) shifting each beat, related to the beat with the mean RMS energy;

iii) for each beat, finding its sub-compartments (splits), as shown in FIG. 18; and iv) utilize dynamic programming to link sub-compartments from different beats (e.g., as illustrated, for example, in Table 1. In some embodiments, the specific dynamic programming of the present invention is configured to identify a series of sub-compartments with each beat and, then link sub-compartments from different beats. In the illustrative examples of Table 1, seeds may be sub-compartments identified in the first most beat (e.g., in the example of Table 1, four (4) sub-compartments of the first beat therefore 4 seeds).

TABLE 1

Each detected beat may have multiple sub-compartments. The purpose of this step is to link between sub compartments from different beats.
For example:
beat 1: sub 1, sub 2, sub 3, sub 4
beat 2: sub 1, sub 2, sub 3
beat 3: sub 1, sub 2, sub 3, sub 4, sub 5
beat 4: sub 1, sub 2, sub 3, sub 4
beat 5: sub 1, sub 2
At step 1, the dynamic programming (DP) may be used to link two sub compartments (sub-compartments in bold are linked in Step 1 of DP):

TABLE 1-continued beat 1: sub 1, sub 2, sub 3, sub 4
beat 2: sub 1, sub 2, sub 3
beat 3: sub 1, sub 2, sub 3, sub 4, sub 5
beat 4: sub 1, sub 2, sub 3, sub 4
beat 5: sub 1, sub 2
The result of Step 1 is a link between sub 1 from beat 1 and sub 2 from beat 2.
In Step 2, the already linked with beat 1 sub-compartment from beat 2 should be linked with
a sub-compartment from beat 3.
For example:
beat 1: sub 1, sub 2, sub 3, sub 4
beat 2: sub 1, sub 2, sub 3
beat 3: sub 1, sub 2, sub 3, sub 4, sub 5
beat 4: sub 1, sub 2, sub 3, sub 4
beat 5: sub 1, sub 2
The iterative process is repeated until all sub-compartments are linked.
For example, below is the outcome of DP process:
beat 1: sub 1, sub 2, *sub 3*, sub 4
beat 2: sub 1, sub 2, *sub 3*
beat 3: sub 1, sub 2, *sub 3*, sub 4, sub 5
beat 4: sub 1, *sub 2*, sub 3, sub 4
beat 5: sub 1, *sub 2*
sub-compartments that are bold, underlined, or italicized are respectively linked.
Sub-compartments that could not be part of a link that is longer than a pre-determined value
are discarded. For example, in the above example, sub-compartments in a regular font are not
linked and therefore discarded since they couldn't be a part of a link that is longer than 4 sub-compartments.

Figure 19A:
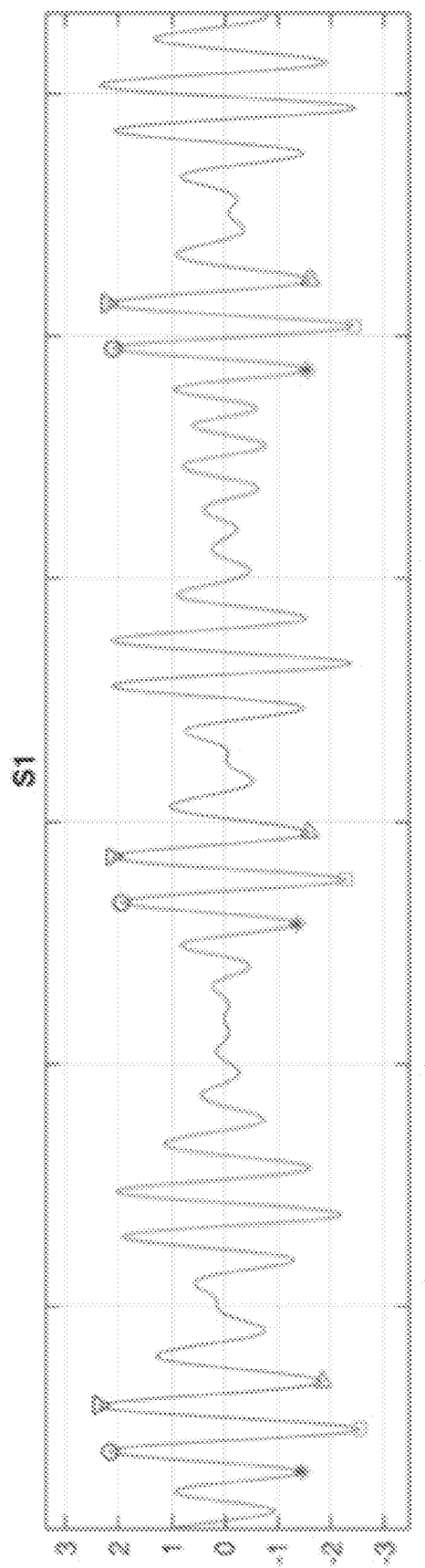
FIGS. 19A and 19B show determined S1 and S2 compartments on a magnified scale within a portion of time samples.
Figure 19B:
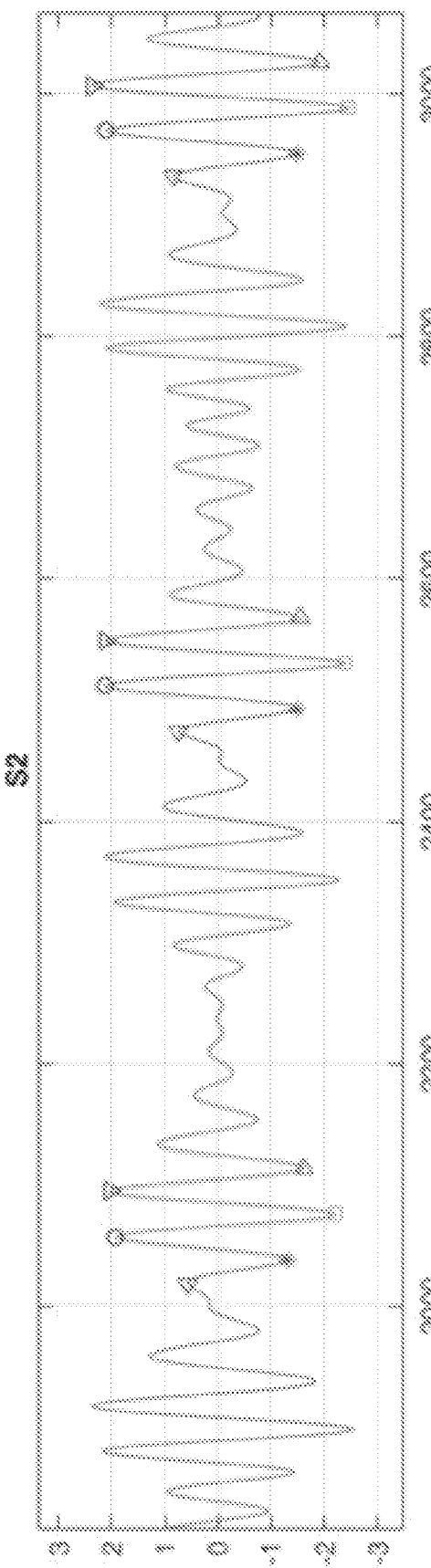

FIGS. 19A-19B show determined S1 and S2 compartments on a magnified scale within a portion of time samples.

Figure 20A:
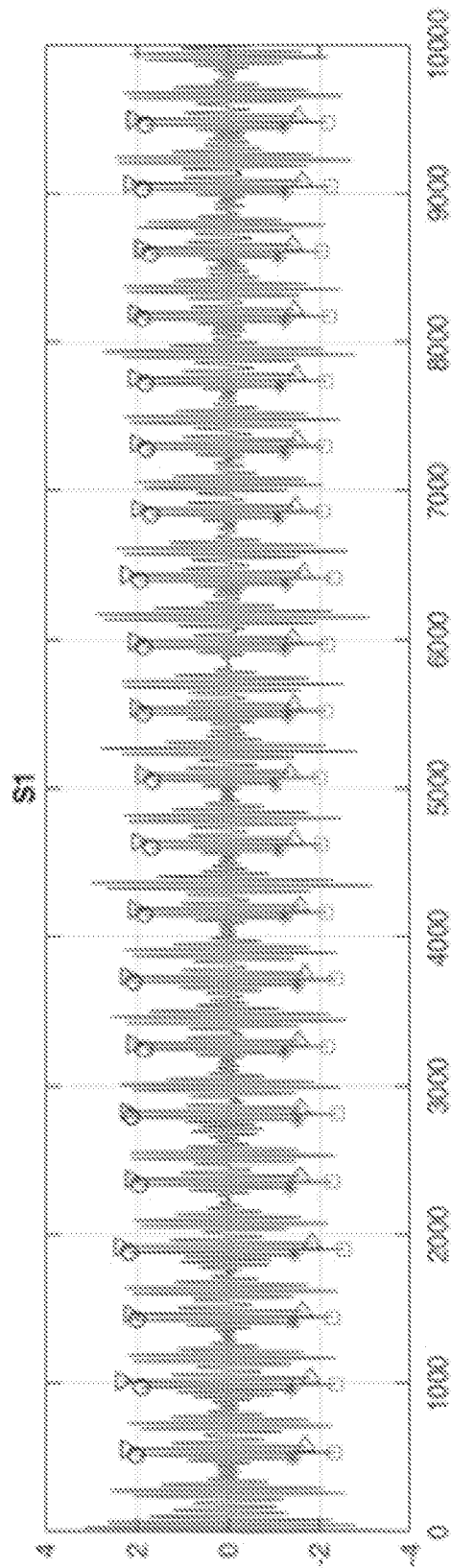
FIGS. 20A and 20B show determined S1 and S2 compartments within a large portion of time samples.
Figure 20B:
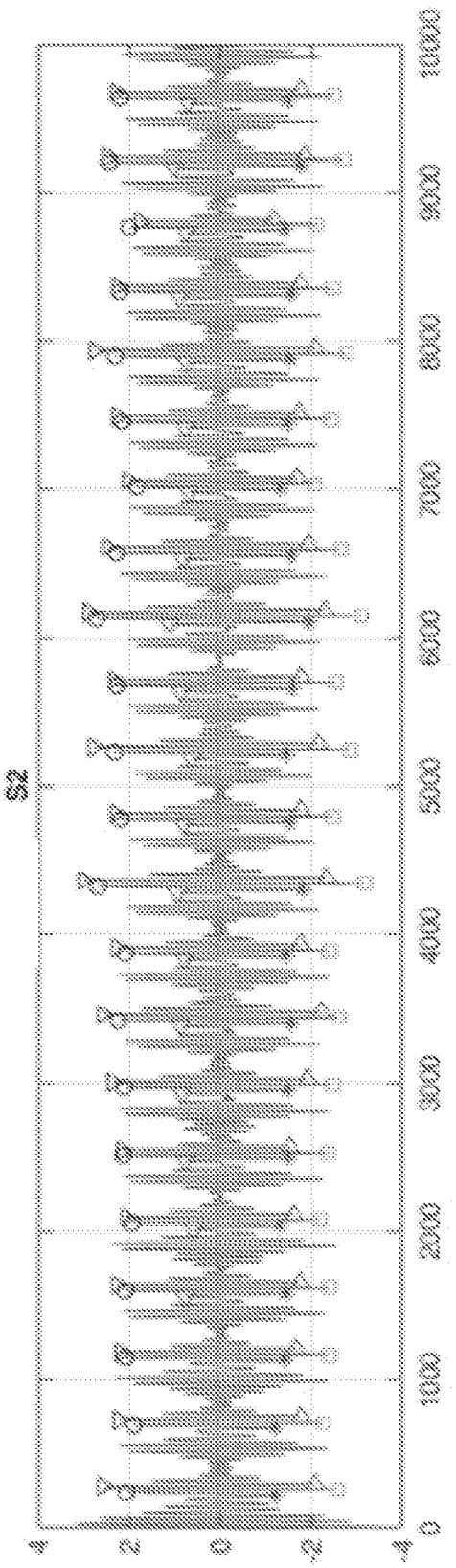

FIGS. 20A-20B show determined S1 and S2 compartments within a large portion of time samples.

Sub-Step 6

In some embodiments, the exemplary Div-Conq algorithm may be programmed to dissect compartments into sub-compartments by:
  i) defining a global reference frame, using: 1) mQRS positions and/or the best sub-compartment (e.g., determined based on a pre-determined scoring);
  ii) aligning sub-compartments; and
  iii) applying a predetermined scoring schema to exclude unacceptable compartments (e.g., sub-compartments that have MAD score exceeds a predetermine threshold such as 50).

Figure 21:
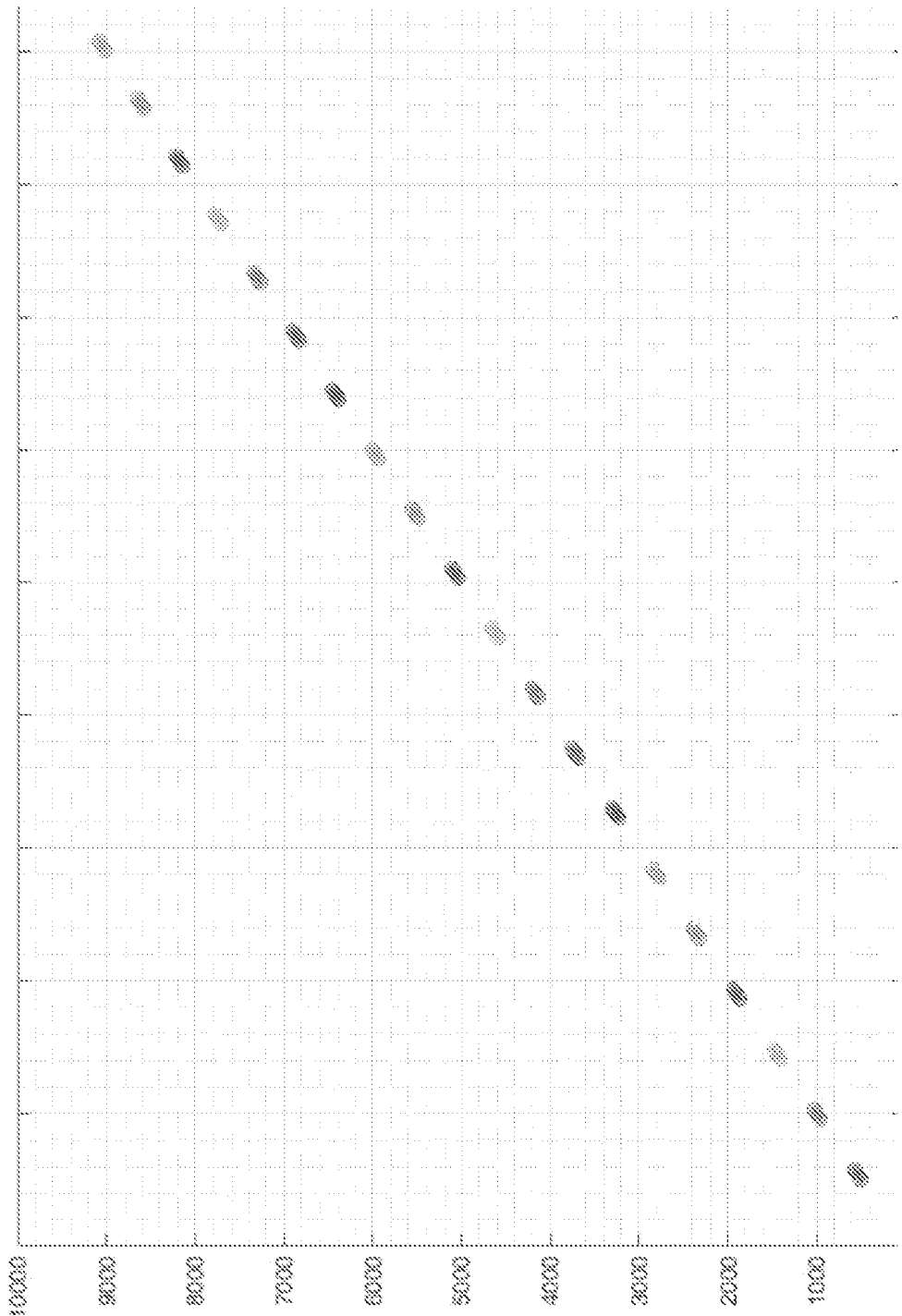
FIG. 21 shows an example of how sub-compartments may be clustered hierarchically into 'beats.'

FIG. 21 shows an example how sub-compartments may be clustered (hierarchal) into 'beats.'

Sub-Step 7

In some embodiments, the exemplary Div-Conq algorithm may be programmed to find an optimal position for each beat by using the clusters ('beats') to find the position of each beat. In some embodiments, the exemplary Div-Conq algorithm may be programmed to utilize dynamic programming with a seed reset. As part of applicable constraints, the applied dynamic programming may be required to account for one or more of the following conditions:
  i) beats must be linked,
  ii) linked beats can vary in length,
  iii) linked beats can start from everywhere in the T3 signal,
  iv) linked beats can end at everywhere in the T3 signal, and
  v) results can span multiple regions of detected beats based on one or more predetermined rule (e.g., a requirement that a minimum link duration to be X beats).

In some embodiments, X may be 4 beats. In some embodiments, X may be 5 beats. In some embodiments, X may be 2. In some embodiments, X may be equal to a number of detected beats in a signal.

In one illustrative example, the exemplary Div-Conq algorithm may detect 100 beats. In some embodiments, in applying DP with the seed reset, the exemplary Div-Conq algorithm may be programmed to select any beat within the 100 beats as the starting beat (in contrast, in the example of Table 1, the starting beat was the first beat that would be identified). Consequently, in some embodiments, the exemplary Div-Conq algorithm may be programmed to utilize the DP with the seed reset to link compartments starting from any detected beat and its respective sub-compartments. In some embodiments, during execution of the DP process the seed could change (i.e., the seed reset) whereas in the illustrative example of Table 1, the seed would be the same during the execution of the DP process.

Sub-Step 8

Figure 22:
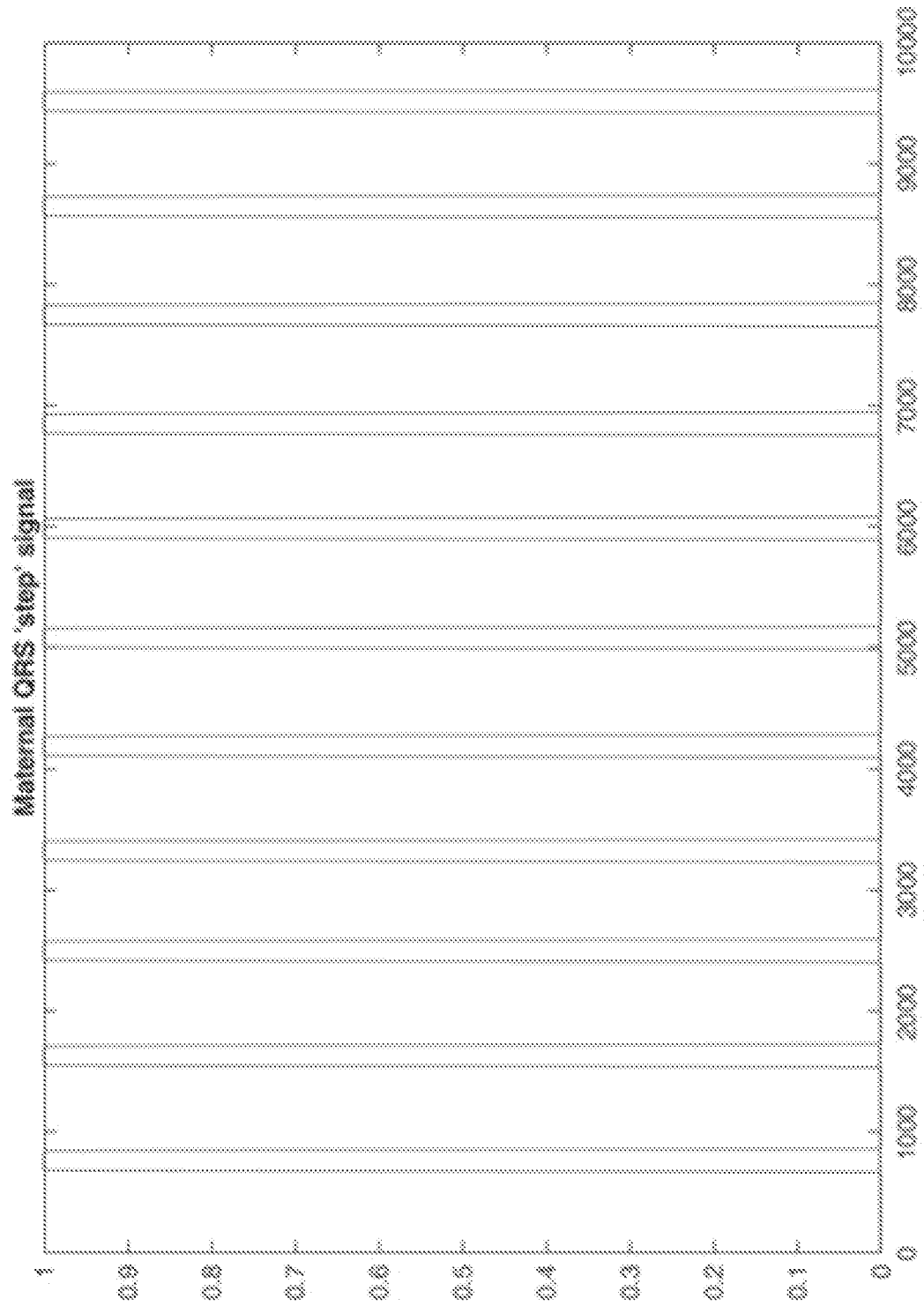
FIG. 22 shows step signals around detected beats.
Figure 23:
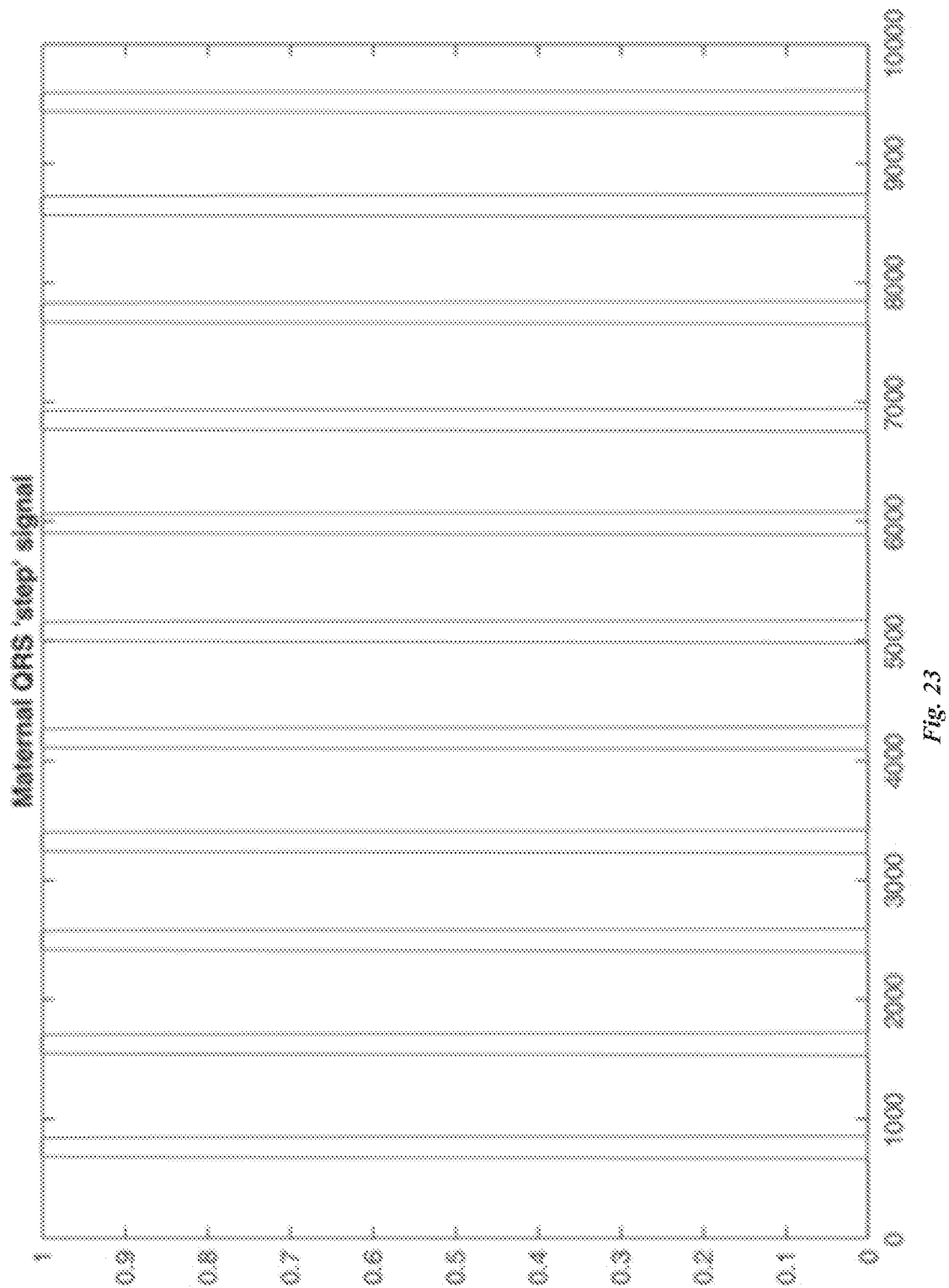
FIG. 23 shows comparison of beat step signals to maternal QRS positions.
Figure 24:
FIG. 24 shows overlaying of beat step signals over maternal QRS positions.

In some embodiments, for each valid compartment, the exemplary Div-Conq algorithm may be further programmed to classify each compartment as maternal or fetal based, at least in part, on reference maternal QRS positions. In some embodiments, the exemplary classification methodology may include at least steps of:
  i) creating step signals around detected beats (for example, shown in FIG. 22),
  ii) comparing the beats step signals (for example, shown in FIG. 22) to the maternal QRS positions (for example, shown in FIG. 23) (for example, FIG. 24 show the overlay of the beats step signals over the maternal QRS positions);
  iii) calculating cross correlation where shift of signals during the calculation of the cross correlation is limited to a lag;
  iv) calculating a mean beat-to-beat duration;
  v) if the correlation is above a predetermined threshold (e.g., 0.7-0.95) and the durations are within a predetermined distance, then such compartment is a maternal signal; and if the correlation is below the predetermined threshold and/or the durations are not within the predetermined distance, the exemplary classification methodology would continue testing; and vi) calculating the normalized DTW of the signals as further detailed herein. For example, if the exemplary Div-Conq algorithm determines two values: value (1) calculated from MQRS and value (2) calculated based on the currently detected beats; then, in some embodiments, the exemplary Div-Conq algorithm may be further programmed to calculate average beat-to-beat duration for both values. In some embodiments, if these durations would be close (e.g., less than 10 bpm) and the correlation would be high, the exemplary Div-Conq algorithm may be further programmed to designate such beats as maternal signals.

Figure 25A:
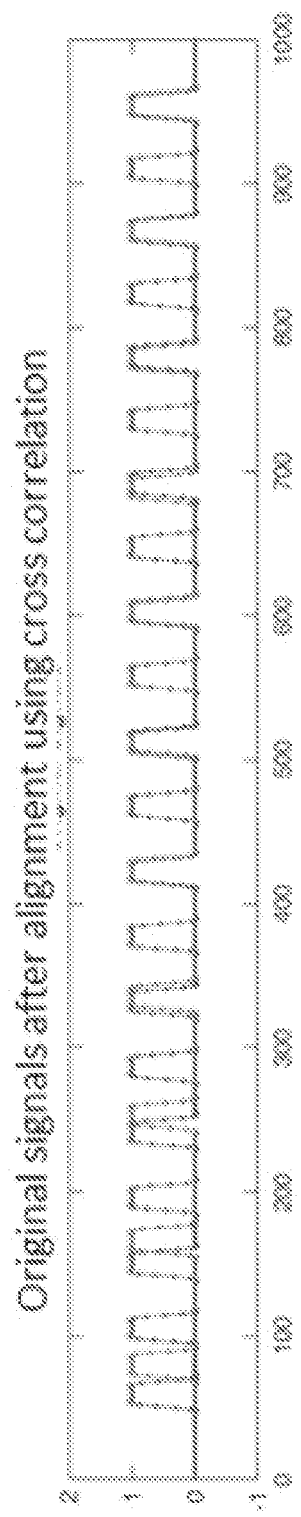
FIG. 25A shows the T3 signals after the alignment based on the cross correlation.
Figure 25B:
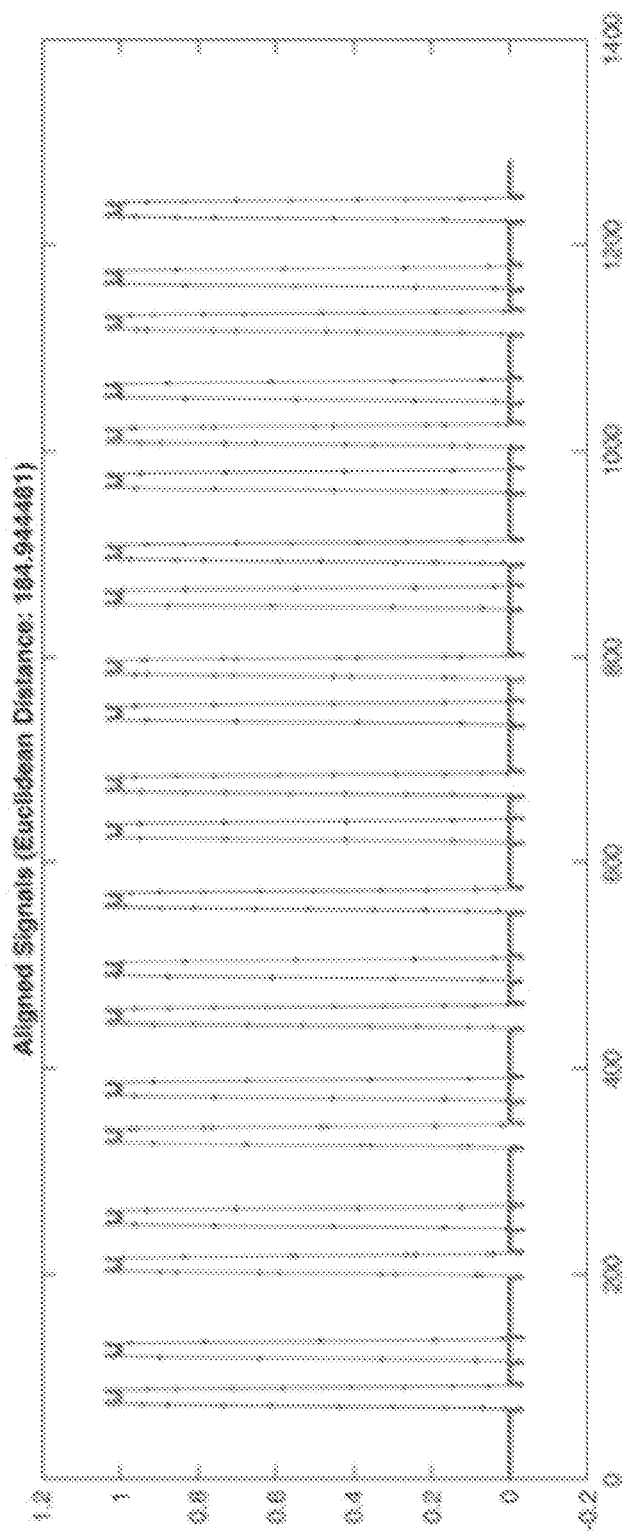
FIG. 25B shows aligned maternal and fetal signals.

For example, in one approach, as the first step of the DTW algorithm, the exemplary Div-Conq algorithm may be further programmed to compare each point in one signal with every point in the second signal, generating a matrix. The second step may be to work through this matrix, starting at the bottom-left corner (corresponding to the beginning of both signals), and ending at the top-right (the end of both signals): for each cell, the cumulative distance is calculated by picking the neighboring cell in the matrix to the left or beneath with the lowest cumulative distance, and adding this value to the distance of the focal cell. When this process is complete, the value in the top-right hand cell may represent the distance between the two signals according to the most efficient pathway through the matrix. FIG. 25A shows the T3 signals after the alignment based on the cross correlation. FIG. 25B shows aligned maternal and fetal signals.

In some embodiments, if the normalized DTW is below a predetermined threshold (e.g., 0.1-0.5) (i.e., it is easy to get from signal a to signal b and vice versa) then such compartment is attributed to maternal signal; and the normalized DTW is above the predetermined threshold, the exemplary classification methodology would continue testing by at least checking if the maternal S1-S2 are mistakenly combined which has resulted in detection of a fetal beat; and when determining that the maternal S1-S2 are not mistakenly combined, identifying such compartment as being associated with the fetal signal.

Sub-Step 9

In some embodiments, the exemplary Div-Conq algorithm may be further programmed to fuse compartments based, at least in part, on grouping all compartments detected in the T3 signal for the same source (maternal or fetal).

In some embodiments, the exemplary Div-Conq algorithm may be further programmed to fuse compartments detected by different signals (e.g., compartments detected by four (4) signals) to produce an array of positions for:
  i) maternal PCG, if available; and
  ii) fetal PCG, if available.
In some embodiments, the array of positions may include a score for each position that may be determined based on a suitable scoring method. For example, the exemplary Div-Conq algorithm may be further programmed to use a scoring scheme that is based on the MAD (Median absolute deviation). For example, the exemplary Div-Conq algorithm may be further programmed to calculate a median distance between members of groups, and then calculate a distance of each member from the median value. For example, "good" groups would have a smaller deviation values, and "bad" groups would have higher values of deviation from the median (e.g., 40).

Sub-Step 10

In some embodiments, the exemplary Div-Conq algorithm may be further programmed to fuse detected peaks from different filters, producing results for maternal and fetal PCGs. For example, each PCG signal may be constructed using different weights for each filter depending on a scoring scheme.

For example, this fusion is based on identified arrays of global peaks for each PCG by utilizing filters that have been selected as having "good" values (i.e., "good" beats) as channels for extracting peaks.

As detailed above, the exemplary Div-Conq algorithm (sub-steps 1-11) may be performed for every 10 seconds interval of T1 signal. If the exemplary Div-Conq algorithm determines that no detection during a particular interval, the exemplary Div-Conq algorithm may be programmed to check if adjacent intervals have detection (e.g., perform backward and forward overlap (e.g., 50%)) and perform the detection again.

Sub-Step 11

In some embodiments, the exemplary Div-Conq algorithm may be further programmed to combine results of the 10 seconds intervals. In some embodiments, the exemplary Div-Conq algorithm may combine results of the 10 seconds intervals based, at least in part, on at least one parameter associated with boundaries of each interval. For example, based on the exemplary partitioning of the T1 signals into 10 seconds windows, the boundaries (close to the beginning and end of each 10 seconds window), might be questionable due to one or more reasons such as if the exemplary Div-Conq algorithm 'cut' a beat that would be present at the boundary (i.e., the center of the beat is exactly at the end of the current window and at the beginning of the next window), the exemplary Div-Conq algorithm might i) detect the beat in both windows, ii) not detect not detect at any window and (iii) detect the beat in only one window. In some embodiments, the exemplary Div-Conq algorithm may be further programmed to check these cases and act accordingly (e.g., eliminating one of cases: case (i) for example).

Figure 26:
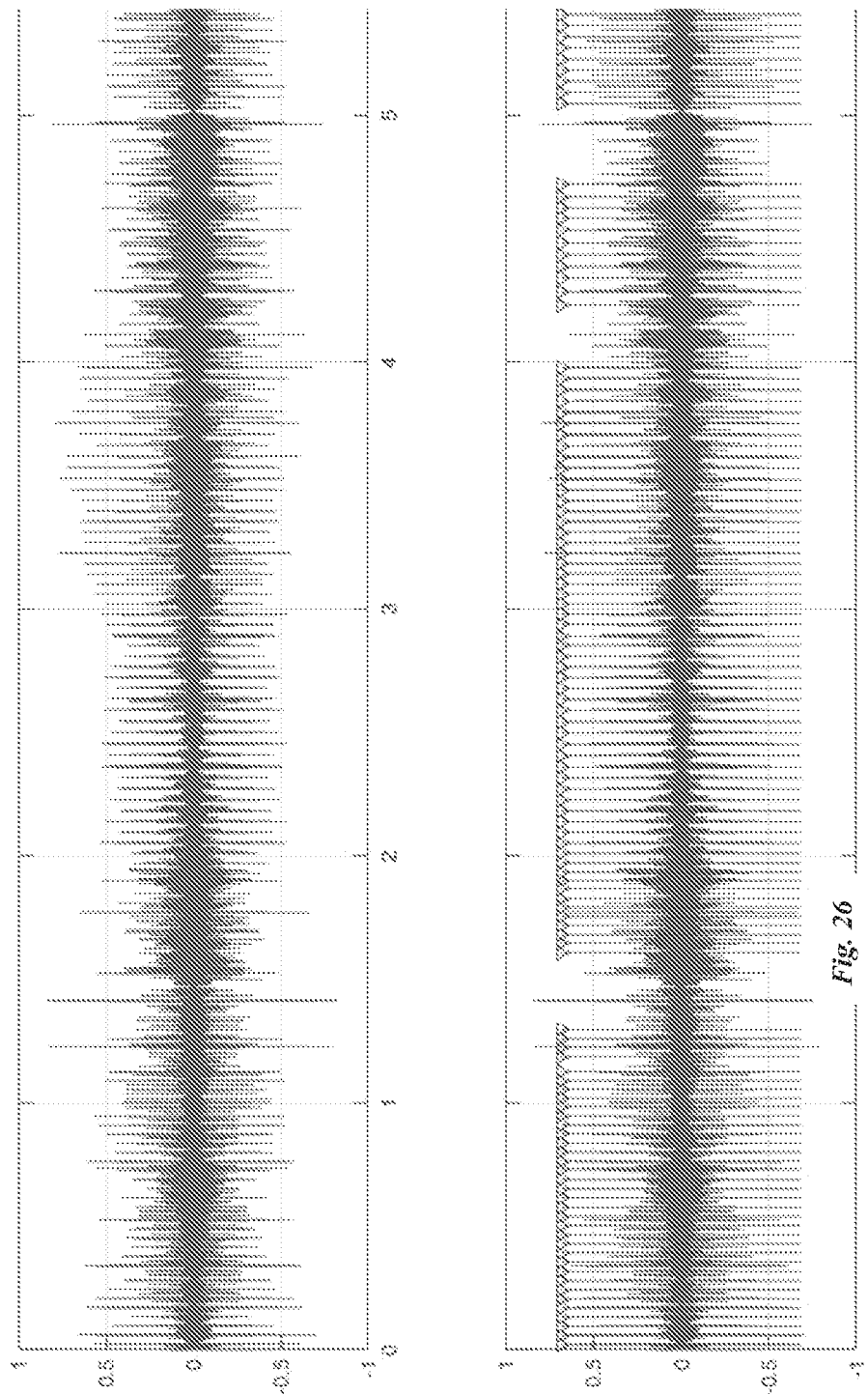
FIG. 26 shows the outcome of detection utilizing the exemplary Div-Conq algorithm.

FIG. 26 shows the outcome of detection utilizing the exemplary Div-Conq algorithm (sub-steps 1-11). Since the exemplary Div-Conq algorithm is tuned for accuracy, the exemplary Div-Conq algorithm would not tolerant to false positives which may result in a decreased detection rate.

III. Illustrative Examples of Applying One or More Algorithms of the Second Type In some embodiments, one or more exemplary methodologies of the present invention include programming the exemplary computer processor so that the exemplary computer processor applies one or more algorithms of the second type to further transform the T1 signal data, for example in parallel, but not limited to, with the processing step 104 of FIG. 1.

Step 1

In some embodiments, an exemplary algorithms of the second type may process T1 signal data in X-minute intervals by at least:
  i) applying a predefined set of filters (e.g., as detailed in U.S. Pat. No. 9,642,544, whose specific disclosure of such filter is hereby incorporated by reference for at least such specific purpose); and
  ii) applying independent component analysis (ICA) (e.g., as detailed in U.S. Pat. No. 9,642,544, whose specific disclosure of such filter is hereby incorporated by reference for at least such specific purpose).

In some embodiments, X may be 10 seconds, 15 seconds, 30 seconds, 1 minute, 2 minutes, 5 minutes, 10 minutes, or any other similarly suitable time period.

In some embodiments, a plurality of bandpass filters may include a L number of bandpass filters, where each bandpass filter outputs a K number of filtered PCG outputs. For example, the predefined set of the plurality of bandpass filters having respective frequency range of 10-45 Hz, 20-50 Hz, 25-65 Hz, 40-80 Hz, 55-95 Hz, and 20-80 Hz.

In some embodiments, the exemplary algorithms of the second type may further include steps for signal enhancement and/or equalization.

In some embodiments, the exemplary algorithms of the second type may be programmed to perform the ICA transformation utilizing a low-power encoding algorithm such as pow3 that is detailed in L. Benini and G. D. Micheli, "State Assignment for Low Power Dissipation," IEEE Journal of Solid-State Circuits, Vol. 30, pp. 258-268, March 1995); and that a greedy algorithm that assigns code bit by bit. At each step, the codes are selected to minimize the number of states with different partial codes.

In some embodiments, the exemplary algorithms of the second type may be programmed to perform the ICA transformation utilizing one or more nonlinearities identified in Table 1, gf is a software object utilized in the ICA transformation.

TABLE 1

| | | |
|---|---|---|
| gf[[1]] | pow3 | $x^3$ |
| gf[[2]] | tanh | $\tanh(x)$ |
| gf[[3]] | gaus | $\exp(-(x)^2/2)$ |
| gf[[4]] | lt0.6 | $(x+0.6)\_-^2$ |
| gf[[5]] | rt0.6 | $(x-0.6)\_+^2$ |
| gf[[6]] | bt | $(x)\_+^2-(x)\_-^2$ |
| gf[[7]] | bt0.2 | $(x-0.2)\_+^2-(x+0.2)\_-^2$ |
| gf[[8]] | bt0.4 | $(x-0.4)\_+^2-(x+0.4)\_-^2$ |
| gf[[9]] | bt0.6 | $(x-0.6)\_+^2-(x+0.6)\_-^2$ |
| gf[[10]] | bt0.8 | $(x-0.8)\_+^2-(x+0.8)\_-^2$ |
| gf[[11]] | bt1.0 | $(x-1.0)\_+^2-(x+1.0)\_-^2$ |
| gf[[12]] | bt1.2 | $(x-1.2)\_+^2-(x+1.2)\_-^2$ |
| gf[[13]] | bt1.4 | $(x-1.4)\_+^2-(x+1.4)\_-^2$ |
| gf[[14]] | bt1.6 | $(x-1.6)\_+^2-(x+1.6)\_-^2$ |

Step 2

In some embodiments, the exemplary algorithms of the second type may be programmed to detect complexes (beats) by at least:
  i) calculating the Hilbert envelope of each signal;
  ii) filtering the Hilbert envelope with a moving average (MA) filter of 300 and 250 mSecond;
  iii) identifying all peaks;
  iv) selecting only peaks that are higher than a predetermine threshold (e.g., 0.1, 0.2, 0.3, etc.);
  v) clustering the selected peaks using k-means clustering (e.g., Lloyd's algorithm or Gaussian mixture models clustering (GMM)) and selecting the best cluster based, at least in part on one of:
    1) normalized width, and/or
    2) normalized prominence;
  vi) selecting the best peaks of the two signals (300/250 msec);
  vii) calculating the Hilbert envelope of each signal;
  viii) filtering the envelope with a MA filter of 100 mSecond; and
  ix) repeating the detection, using dynamic programing with the previously detected peaks as seeds (fine tuning the detection).

Step 3

In some embodiments, the exemplary algorithms of the second type may be further programmed to score and classify complexes (beats) by at least:
  i) applying a suitable scoring scheme to all of the detected complexes for each signal, and
  ii) classifying the complexes as maternal, fetal, or noise.

In detecting maternal beats, the exemplary algorithms of the second type may be programmed to select results of the signals with the best score. In some embodiments, the exemplary algorithms of the second type may be programmed to combine all detected maternal complexes.

In detecting fetal beats, the exemplary algorithms of the second type may be programmed to also select results of the signals with the best score. In some embodiments, the exemplary algorithms of the second type may be programmed to combine all detected fetal complexes.

IV. Illustrative Examples of Applying One or More Algorithms of the Third Type

In some embodiments, one or more exemplary methodologies of the present invention include programming the exemplary computer processor so that the exemplary computer processor applies one or more algorithms of the third type that is programmed accept as input 1) the output from the exemplary algorithm of the first type and 2) the output from the exemplary algorithm of the second type, as shown by the processing step 105 of FIG. 1.

In some embodiments, at Step 1, the exemplary algorithm of the third type may be programmed to determine a score for each detected beat for each algorithm of the first type and the second type, For example, the exemplary algorithm of the third type may be programmed to calculate a mean score for beats in 5 seconds intervals and, based on a desired value for the mean score (e.g., 0.2), include beats of the respective algorithm type.

At Step 2, the exemplary algorithm of the third type may be programmed to remove beats that are too near each other (e.g., by estimating a local beat-to-beat interval and calculating a local threshold that may be a half of the locally estimated beat-to-beat interval).

Figure 27A:
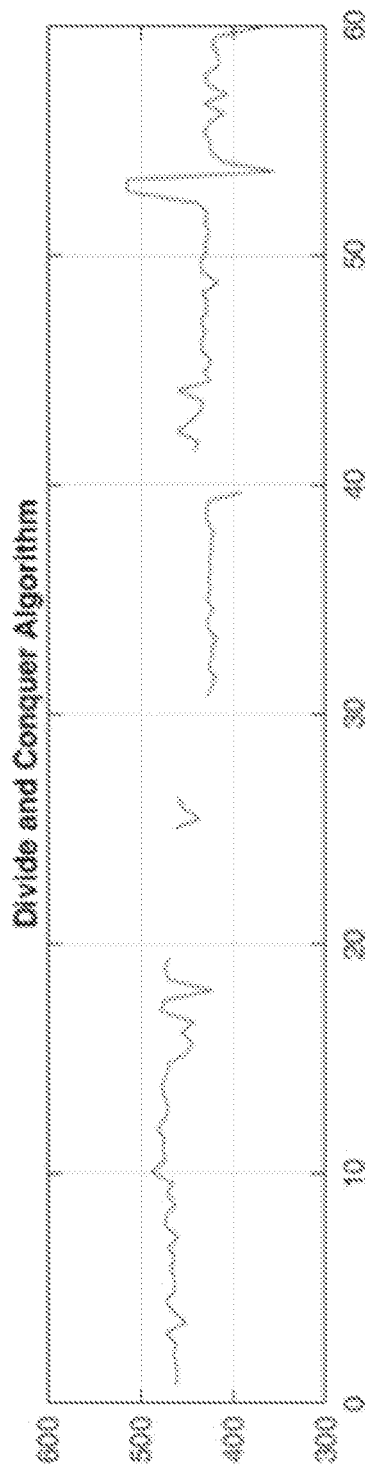
FIG. 27A shows an illustrative output of the exemplary algorithm of the first type.
Figure 27B:
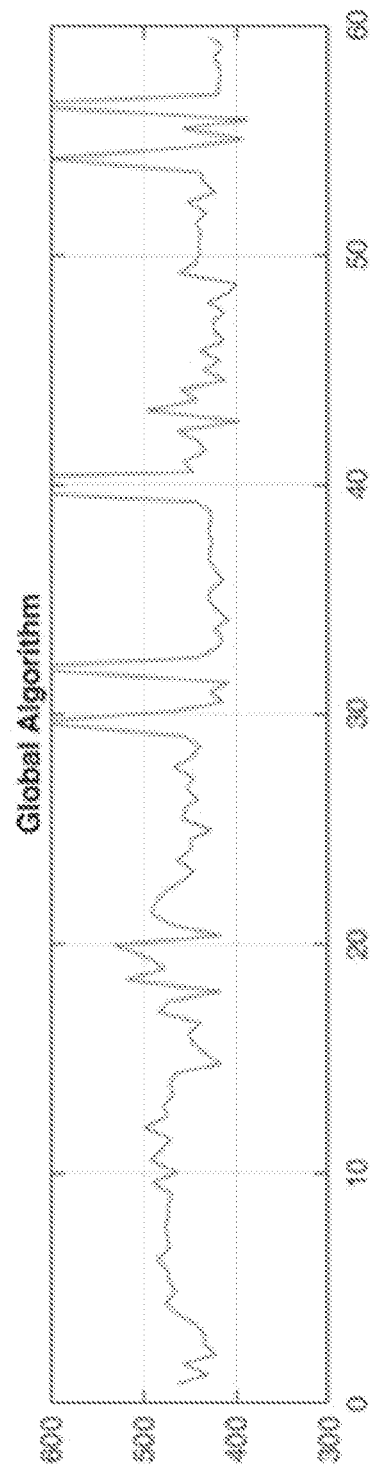
FIG. 27B shows an illustrative output of the exemplary algorithm of the second type.
Figure 27C:
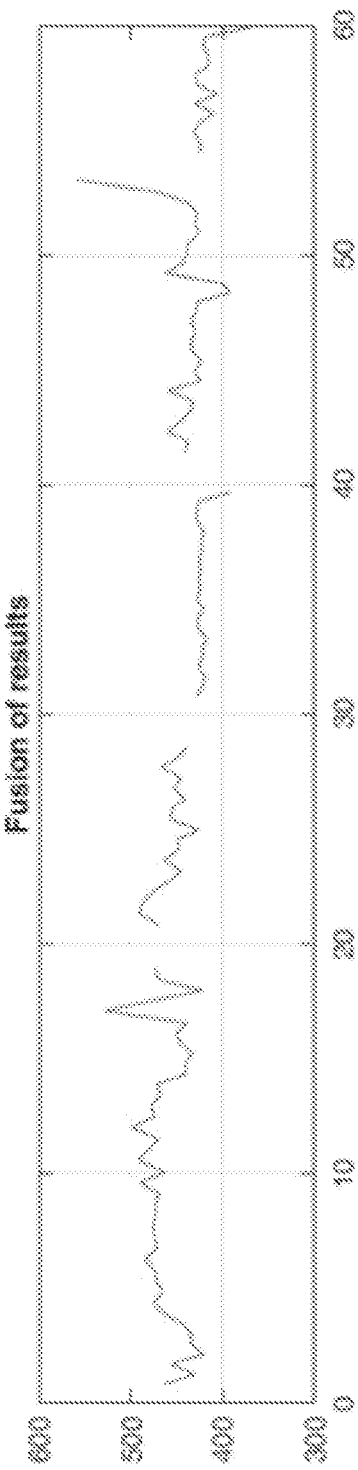
FIG. 27C shows an illustrative output of the exemplary algorithm of the third type.

FIG. 27A shows an illustrative output of the exemplary algorithm of the first type. FIG. 27B shows an illustrative output of the exemplary algorithm of the second type. FIG. 27C shows an illustrative output of the exemplary algorithm of the third type.

Figure 28:
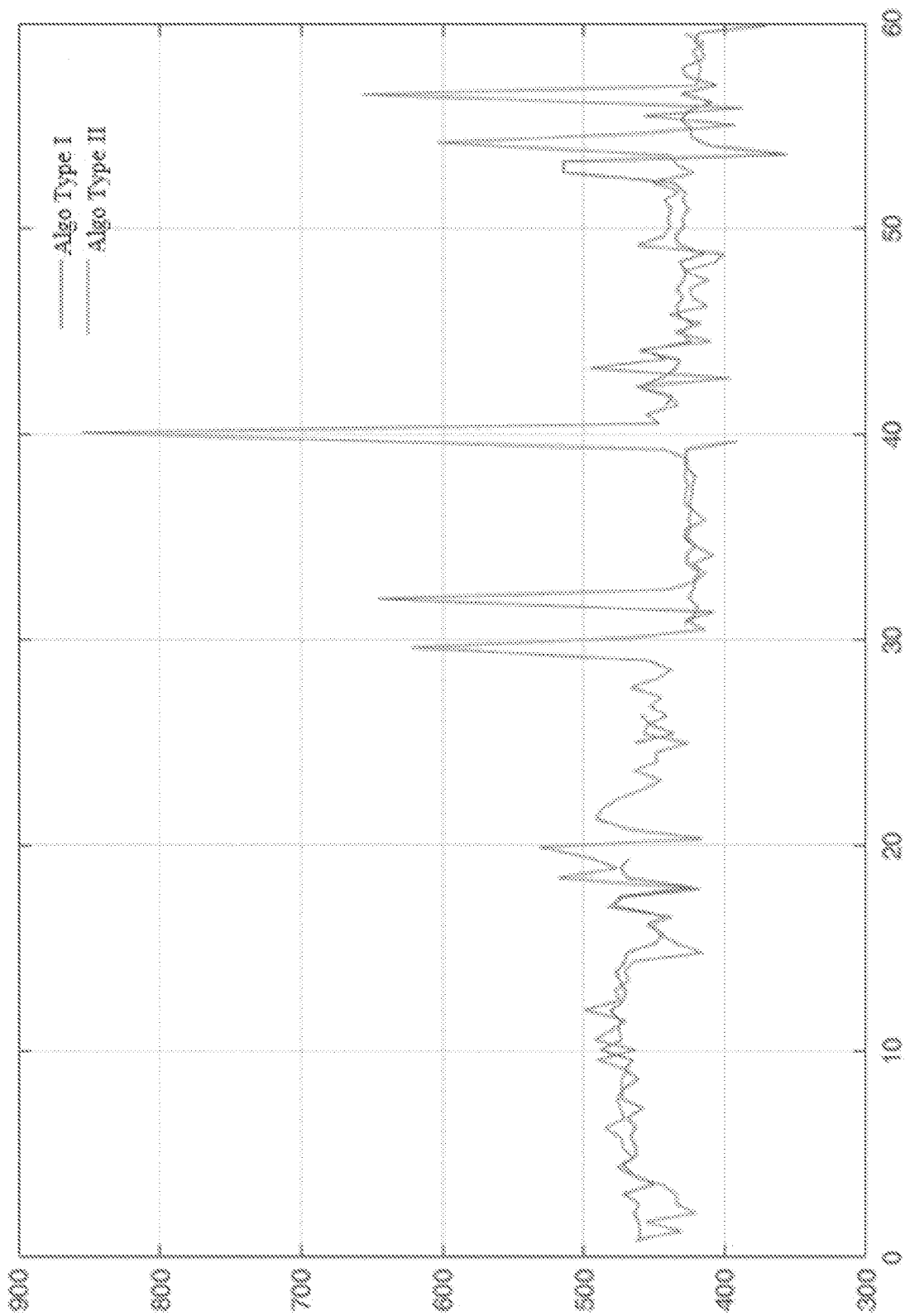
FIG. 28 shows a graph combining the illustrative output of the exemplary algorithm of the first type with the illustrative output of the exemplary algorithm of the second type.

In contrast, FIG. 28 shows a graph combining the illustrative output of the exemplary algorithm of the first type with the illustrative output of the exemplary algorithm of the second type.

Of note, the embodiments described herein may, of course, be implemented using any appropriate hardware and/or computing software languages. In this regard, those of ordinary skill in the art are well versed in the type of computer hardware that may be used, the type of computer programming techniques that may be used (e.g., object oriented programming), and the type of computer programming languages that may be used (e.g., C++, Basic, AJAX, Javascript). The aforementioned examples are, of course, illustrative and not restrictive.

While a number of embodiments of the present invention have been described, it is understood that these embodiments are illustrative only, and not restrictive, and that many modifications may become apparent to those of ordinary skill in the art, including that the inventive methodologies, the inventive systems, and the inventive devices described herein can be utilized in any combination with each other. Further still, the various steps may be carried out in any desired order (and any desired steps may be added and/or any desired steps may be eliminated).

We claim:

1. A computer-implemented method, comprising:
  receiving, by at least one computer processor executing specific programmable instructions configured for the method, a plurality of raw phonocardiogram (PCG) data inputs, each of the plurality of raw PCG data inputs being received from a corresponding one of a plurality of acoustic sensors;

applying, by the at least one computer processor, at least one binary classification technique to each of the plurality of raw PCG data inputs signals to generate a respective plurality of filtered PCG data inputs, by filtering each respective raw PCG data input based, at least in part, on one or more of:
   i) a root-mean-square (RMS) value of each respective raw PCG data input,
   ii) a RMS value of a first derivative of each respective raw PCG data input,
   iii) a variance value of each respective raw PCG data input, and
   iv) any combination thereof;

applying, by the at least one computer processor, at least one divide-and-conquer (Div-Conq) algorithm to detect heartbeat compartments in each of the plurality of the filtered PCG data inputs based, at least on part, on assumptions that noise signals are non-stationary over a one-minute time interval and that S1-S2 alternation acoustic signals are non-stationary over the one-minute time interval;

classifying each compartment of the heartbeat compartments in each of the plurality of the filtered PCG data input as a maternal compartment or a fetal compartment based at least on a plurality of referenced maternal QRS positions;

combining a plurality of maternal compartments to identify at least one actual maternal heartbeat;

combining a plurality of fetal compartments to identify at least one actual fetal heartbeat; and outputting at least one visual indication corresponding to at least one of (a) the at least one actual maternal heartbeat and (b) the at least one actual fetal heartbeat.

2. The method of claim 1, wherein the Div-Conq algorithm includes at least the steps of:
   i) filtering each of the pre-processed PCG signals using at least one digital filter to generate a plurality of filtered PCG signals, each of the plurality of the filtered PCG signals being generated based on a corresponding one of the pre-processed PCG signals;
   ii) segmenting each of the filtered PCG signals into PCG signal segments having a predetermined length;
   iii) detecting compartments in the PCG signal segments, wherein the step of detecting compartments comprises the sub-steps of:
     a) identifying related beats;
     b) shifting each beat, related to the beat with the mean RMS energy;
     c) finding sub-compartments of each beat; and
     d) linking sub-compartments from different beats using dynamic programming to generate an indication of a heartbeat.

3. The method of claim 2, wherein the predetermined length is 10 seconds.

4. The method of claim 2, wherein the compartments include at least one S1, at least one S2, or at least one S1 and at least one S2.

5. The method of claim 1, wherein the compartments include at least one of a fetal heartbeat, a maternal heartbeat, and/or both a maternal heartbeat and a fetal heartbeat.

6. The method of claim 1, wherein the at least one digital filter includes a complex Hilbert transform filter.

7. The method of claim 2, wherein if more than one group of compartments have been detected, the Div-Conq algorithm further comprises testing the groups of compartments.

8. The method of claim 7, wherein the step of testing the groups of compartments includes a mean absolute deviation process.

9. The method of claim 1, wherein the step of detecting compartments in the PCG signal segments further comprises the sub-step of dissecting compartments into sub-compartments.

10. The method of claim 9, wherein the dissecting compartments into sub-compartments comprises:
   a) defining a global reference frame;
   b) aligning sub-compartments; and
   c) applying a predetermined scoring schema to exclude unacceptable sub-compartments.

11. The method of claim 10, wherein the defining a global reference frame is based on mQRS positions.

12. The method of claim 10, wherein the defining a global reference frame is based on a best sub-compartment.

13. The method of claim 12, wherein the best sub-compartment is identified by a pre-determined scoring.

14. The method of claim 10, wherein the unacceptable compartments are identified as compartments having a mean absolute deviation that is greater than a mean absolute deviation threshold.

15. The method of claim 14, wherein the mean absolute deviation threshold is 50.

16. The method of claim 1, wherein the step of detecting compartments is performed using a binary SVM classifier.

\* \* \* \* \*